US012661448B2

(12) United States Patent
Diaz et al.

(10) Patent No.: US 12,661,448 B2
(45) Date of Patent: Jun. 23, 2026

(54) INJECTION SYSTEM AND METHOD

(71) Applicant: CREDENCE MEDSYSTEMS, INC., Menlo Park, CA (US)

(72) Inventors: Stephen H. Diaz, Palo Alto, CA (US); Jeff Tillack, Foster City, CA (US); Alan E. Shluzas, San Carlos, CA (US)

(73) Assignee: Credence Medsystems, Inc., Menlo Park, CA (US)

( * ) Notice: Subject to any disclaimer, the term of this patent is extended or adjusted under 35 U.S.C. 154(b) by 695 days.

(21) Appl. No.: 18/098,295

(22) Filed: Jan. 18, 2023

(65) Prior Publication Data

US 2023/0248913 A1 Aug. 10, 2023

Related U.S. Application Data

(60) Provisional application No. 63/300,394, filed on Jan. 18, 2022.

(51) Int. Cl.
A61M 5/19 (2006.01)
A61M 5/20 (2006.01)
(Continued)

(52) U.S. Cl.
CPC ............ A61M 5/19 (2013.01); A61M 5/2066 (2013.01); A61M 5/2448 (2013.01);
(Continued)

(58) Field of Classification Search
CPC .... A61M 5/19; A61M 5/2066; A61M 5/2448; A61M 5/284; A61M 5/31515;
(Continued)

(56) References Cited

U.S. PATENT DOCUMENTS 5,298,024 A * 3/1994 Richmond ........ A61M 5/31596
604/88
5,478,323 A 12/1995 Westwood
(Continued)

FOREIGN PATENT DOCUMENTS

WO WO 2018134211 7/2018
WO WO 2019246435 12/2019
WO WO 2022006341 1/2022

OTHER PUBLICATIONS

PCT International Search Report and Written Opinion for International Appln. No. PCT/2023/010991, Applicant Credence Medsystems, Inc., dated Jun. 5, 2023.
(Continued)

*Primary Examiner* — Tasnim Mehjabin Ahmed
(74) *Attorney, Agent, or Firm* — Vista IP Law Group, LLP

(57) ABSTRACT

An injection system includes an injection system body defining a proximal opening at a proximal end thereof and a distal needle interface at a distal end thereof. The system also includes proximal and distal stopper members disposed in the injection system body, forming a proximal drug chamber between the proximal and distal stopper members and a distal drug chamber between the distal stopper member and the distal end of the injection system body. The system further includes a plunger member configured to be manually manipulated to insert the proximal stopper member relative to the injection system body. Moreover, the system includes a valve forming an openable barrier between the distal needle interface and at least a portion of the distal drug chamber. The valve is configured to allow flow from the portion of the distal drug chamber to the distal needle interface with increased pressure in the distal drug chamber.

25 Claims, 30 Drawing Sheets

(51) Int. Cl.

| | |
|---|---|
| *A61M 5/24* | (2006.01) |
| *A61M 5/28* | (2006.01) |
| *A61M 5/315* | (2006.01) |
| *A61M 5/32* | (2006.01) |
| *A61M 5/34* | (2006.01) |
| *A61M 39/24* | (2006.01) |
| *A61M 5/31* | (2006.01) |

(52) U.S. Cl.
CPC ........ *A61M 5/284* (2013.01); *A61M 5/31515* (2013.01); *A61M 5/31596* (2013.01); *A61M 5/3234* (2013.01); *A61M 5/329* (2013.01); *A61M 5/3294* (2013.01); *A61M 5/34* (2013.01); *A61M 39/24* (2013.01); *A61M 2005/3128* (2013.01)

(58) Field of Classification Search
CPC ............ A61M 5/31596; A61M 5/3234; A61M 5/329; A61M 5/3294; A61M 5/34; A61M 39/24; A61M 2005/3128; A61M 2005/3139; A61M 2005/1787; A61M 2039/242; A61M 2039/246
See application file for complete search history.

(56) References Cited

U.S. PATENT DOCUMENTS

| | | | | |
|---|---|---|---|---|
| 5,599,312 A | * | 2/1997 | Higashikawa | .......... A61M 5/19 604/218 |
| 2024/0358927 A1 | * | 10/2024 | Baviskar | .......... A61M 5/31596 |

OTHER PUBLICATIONS

Foreign First Examination Report for IN Patent Appln. No. 202447053590 dated Mar. 17, 2026.

* cited by examiner

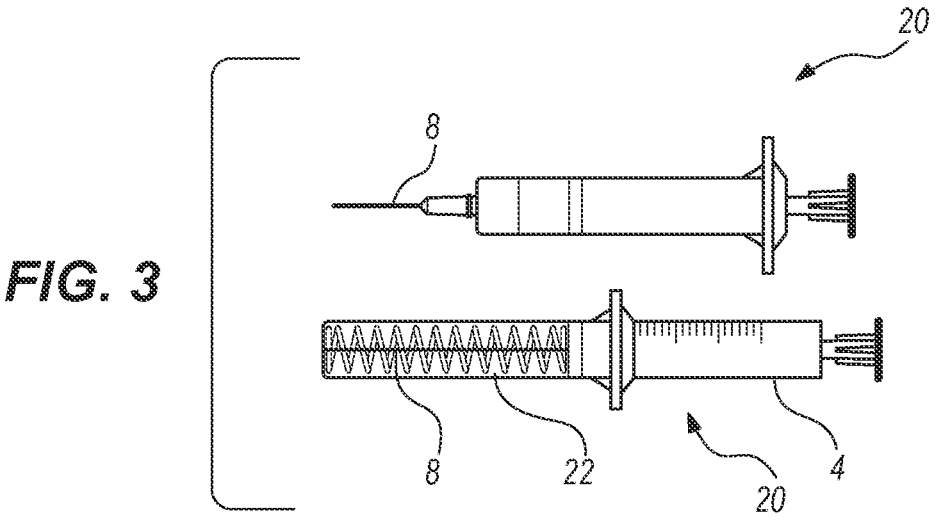
*FIG. 3*
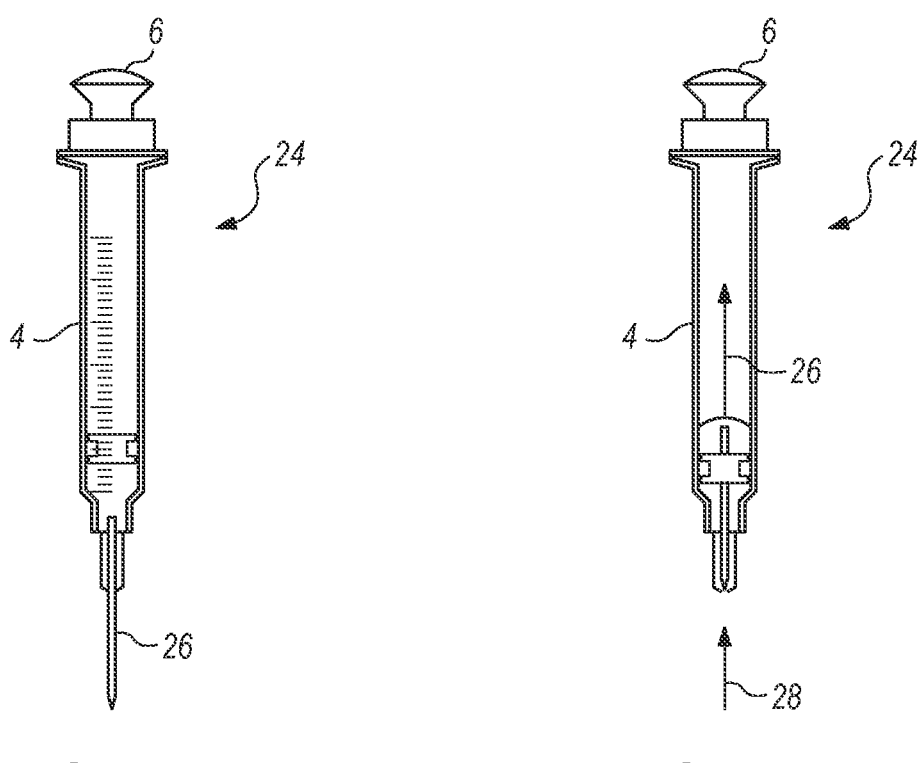
*FIG. 4A*          *FIG. 4B*

1

INJECTION SYSTEM AND METHOD

The present application claims priority to U.S. Provisional Patent Application Ser. No. 63/300,394, filed on Jan. 18, 2022 and entitled "INJECTION SYSTEM AND METHOD." This application includes subject matter similar to the subject matter described in the following co-owned U.S. patent applications: (1) U.S. Utility patent application Ser. No. 14/321,706, filed Jul. 1, 2014 and issued as U.S. Pat. No. 9,814,842 on Nov. 14, 2017 and entitled "SAFETY SYRINGE"; (2) U.S. Utility patent application Ser. No. 14/543,787, filed Nov. 17, 2014 and issued as U.S. Pat. No. 10,300,217 on May 28, 2019 under and entitled "SYSTEM AND METHOD FOR DRUG DELIVERY WITH A SAFETY SYRINGE"; (3) U.S. Utility patent application Ser. No. 14/696,342, filed Apr. 24, 2015, and issued as U.S. Pat. No. 10,010,677 on Jul. 7, 2018 and entitled "SYSTEM AND METHOD FOR SAFETY SYRINGE"; (4) U.S. Utility patent application Ser. No. 15/801,239, filed on Nov. 1, 2017 and issued as U.S. Pat. No. 10,926,038 on Feb. 23, 2021 and entitled "SYSTEM AND METHOD FOR SAFETY SYRINGE"; (5) U.S. Utility patent application Ser. No. 15/801,259, filed on Nov. 1, 2017, and issued as U.S. Pat. No. 10,864,330 on Dec. 15, 2020 and entitled "SYSTEM AND METHOD FOR SAFETY SYRINGE"; (6) U.S. Utility patent application Ser. No. 15/801,281 filed on Nov. 1, 2017 and issued as U.S. Pat. No. 10,912,894 on Feb. 9, 2021 and entitled "CARTRIDGE SAFETY INJECTION SYSTEM AND METHODS"; (7) U.S. Utility patent application Ser. No. 15/801,304 filed on Nov. 1, 2017 and issued as U.S. Pat. No. 10,960,144 on Mar. 30, 2021 and entitled "SYSTEM AND METHOD FOR SAFETY SYRINGE"; (8) U.S. patent application Ser. No. 16/798,188, filed on Feb. 21, 2020 and entitled "SYSTEM AND METHOD FOR SAFETY SYRINGE"; (9) U.S. Utility patent application Ser. No. 16/435,429 filed on Jun. 7, 2019 and entitled "SYSTEM AND METHOD FOR SAFETY SYRINGE"; (10) U.S. Utility patent application Ser. No. 16/837,835, filed Apr. 1, 2020 and entitled "POLYMERIC INJECTION SYSTEMS"; (11) U.S. patent application Ser. No. 16/908, 531 filed on Jun. 22, 2020 and entitled "INJECTION SYSTEM AND METHOD"; (12) U.S. Provisional Patent Application Ser. No. 62/904,988 filed on Sep. 24, 2019 and entitled "SYSTEM AND METHOD FOR SAFETY SYRINGE"; (13) U.S. Provisional Patent Application Ser. No. 63/094,313 filed on Oct. 20, 2020 and entitled "RETRACTION MECHANISM FOR SAFE INJECTION SYSTEM"; (14) U.S. Provisional Patent Application Ser. No. 62/682,381, filed on Jun. 8, 2018 and entitled "SYSTEM AND METHOD FOR SAFETY SYRINGE"; (15) U.S. Provisional Patent Application Ser. No. 62/729,880, filed on Sep. 11, 2018 and entitled "SYSTEM AND METHOD FOR SAFETY SYRINGE"; (16) U.S. Provisional Patent Application Ser. No. 63/094,313 filed on Oct. 20, 2020 and entitled "RETRACTION MECHANISM FOR SAFE INJECTION SYSTEM"; (17) U.S. Provisional Patent Application Ser. No. 63/046,517, filed on Jun. 30, 2020 and entitled "SYSTEM AND METHOD FOR SAFETY SYRINGE"; (18) U.S. Provisional Patent Application Ser. No. 63/156,264, filed on Mar. 3, 2021 and entitled "SYSTEM AND METHOD FOR SAFETY SYRINGE"; and (19) U.S. Provisional Patent Application Ser. No. 63/193,466, filed on May 26, 2021 and entitled "SYSTEM AND METHOD FOR SAFETY SYRINGE". The contents of the applications and patents identified herein are fully incorporated herein by reference as though set forth in full.

FIELD OF THE DISCLOSURE

The present disclosure relates generally to injection systems, devices, and processes for facilitating various levels of control over fluid infusion, and more particularly to systems and methods related to multiple chamber injection systems, with or without safety features, in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possibly malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

In some cases, multi-component injection systems may mix injectable components (e.g., liquids and/or powders) before injection. Some systems utilize a single injection device to draw a component liquid from one container and inject the liquid component into another container to solubilize the dry component therein. The solubilized dry component is then drawn into the injection device for injection into a patient. Such systems require much handling of unsheathed needles, leading to unnecessary exposure of a user to one or more uncapped needles. Further, manually the liquid component from one container to another can result in incomplete transfer of the liquid component and affect the ratio of the components in the final mixed injectable. Moreover, accessing and manipulating multiple containers of components complicates the injection process, thereby increasing the risk of user error. Accordingly, there exists a need for multi-component injection systems that simplify the manual accessing and mixing of multiple components from multiple containers.

These limitations are addressed by multiple chamber injection systems configured to mix and injection multiple components as disclosed in U.S. Utility patent application Ser. Nos. 14/696,342 and 15/801,259, which were previously incorporated by reference herein. However, there remains a need for precise control of multiple chamber injection systems for accurate handling, mixing, and delivery of multi-component injectables.

In addition, an increasing number of injectable liquids (e.g., medicines) have yet another requirement that time of exposure of the injectable liquid to metals (e.g., stainless steel of a needle) be minimized.

It is also desirable to incorporate needle stick prevention technology into the injection system. The ability to retract the sharp end of the needle at least partially inside of the syringe protects the person giving the injection and the patient from inadvertent needle stick injuries.

There is a need for injection systems which address the shortcomings of currently-available configurations. In particular, there is a need for multiple chamber safety injection solutions with precise control, which may utilize the existing and relatively well-controlled supply chain of conventionally delivered prefilled syringe assemblies such as those described in reference to FIGS. 5A and 5B.

SUMMARY

Embodiments are directed to injection systems. In particular, the embodiments are directed to multiple chamber safe injection systems with precise control of handling, mixing, and delivery of multi-component injectables.

In one embodiment, an injection system includes an injection system body defining a proximal opening at a proximal end thereof and a distal needle interface at a distal end thereof. The system also includes proximal and distal stopper members disposed in the injection system body, forming a proximal drug chamber between the proximal and distal stopper members and a distal drug chamber between the distal stopper member and the distal end of the injection system body. The system further includes a plunger member configured to be manually manipulated to insert the proximal stopper member relative to the injection system body. Moreover, the system includes a valve forming an openable barrier between the distal needle interface and at least a portion of the distal drug chamber. The valve is configured to allow flow from the portion of the distal drug chamber to the distal needle interface with increased pressure in the distal drug chamber.

In one or more embodiments, the system also includes an elongate fluid conveying member, and the valve is configured to stabilize the elongate fluid conveying member in the distal drug chamber. The valve may define a central opening and may include a central seal. The fluid conveying member may be configured to pass through the central opening, and the central seal may be configured to form a fluid tight seal against an outer longitudinal surface of the fluid conveying member. The valve may define a distally facing funnel configured to guide a proximal end of the fluid conveying member through the central seal during assembly of the injection system. The valve may define a distally facing circumferential wall configured to provide a space between the valve and the distal end of the injection system body.

In one or more embodiments, the valve includes a circumferential gasket configured to form a fluid tight seal with an inner surface of the injection system body in the distal drug chamber. The circumferential gasket may be made from an elastic material. The elastic material may be rubber, thermoplastic elastomer, butyl rubber, or polyisoprene elastomer. The circumferential gasket may be configured to couple the valve to the inner surface of the injection system body. The valve may include a port configured to be opened by the increased pressure in the distal drug chamber.

In one or more embodiments, the valve includes a rigid portion and an elastic portion. The rigid portion may be made from cyclic olefin copolymer. The elastic portion may be made from rubber, thermoplastic elastomer, butyl rubber, or polyisoprene elastomer. The elastic portion may include an annular flap configured to be disposed adjacent a distal surface of the rigid portion, and a circumferential gasket extending from and outer circumference of the annular flap. The circumferential gasket may be configured to form a fluid tight seal with an inner surface of the injection system body in the distal drug chamber.

In one or more embodiments, the rigid portion may include an annular portion. The annular portion may define a port extending therethrough, and the port may be configured to be removably sealed by the annular flap of the elastic portion. The annular flap of the elastic portion may be configured such that the annular flap is biased to removably seal the port. The increased pressure in the distal drug chamber may move the annular flap away from the port defined by the annular portion of the rigid portion, thereby unsealing the port. The annular portion may define a raised annular wall surrounding the port and extending a distally from a distal surface of the annular portion. The annular portion may define a distally extending dome. The rigid portion may include a distally extending portion coupled to an annular portion. The distally extending portion may be configured to interfere with the distal needle interface to provide a space between the valve and the distal end of the injection system body.

In one or more embodiments, the distally extending portion is configured to interfere with the distal needle interface to couple the valve to the injection system body such that a distal surface of a circumferential gasket of the valve is in contact with the distal end of the injection system body. The circumferential gasket may be configured to form a fluid tight seal with an inner surface of the distal end of the injection system body. The circumferential gasket may have an outer circumference smaller than an inner circumference of the injection system body. The distally extending portion may be configured to interfere with the distal needle interface to provide a space between the valve and the distal end of the injection system body.

In another embodiment, an injection system includes an injection system body defining a proximal opening at a proximal end thereof and a distal needle interface at a distal end thereof. The system also includes proximal and distal stopper members disposed in the injection system body, forming a proximal drug chamber between the proximal and distal stopper members and a distal drug chamber between the distal stopper member and the distal end of the injection system body. The system further includes a plunger member configured to be manually manipulated to insert the proximal stopper member relative to the injection system body. Moreover, the system includes an elongate fluid conveying member configured to at least partially pierce the proximal stopper member to form a flow path from the distal drug chamber to the proximal drug chamber, the elongate fluid conveying member defining a circumferential shoulder. In addition, the system includes and insert configured to be disposed in the proximal stopper member. The insert includes a distally facing funnel and a pair of fingers configured to interfere with the circumferential shoulder on the elongate fluid conveying member to temporarily prevent distally directed motion of the proximal stopper member relative to the elongate fluid conveying member while the flow path from the distal drug chamber to the proximal drug chamber is open.

In one or more embodiments, the funnel is made from cyclic olefin copolymer. The pair of fingers may be made from a metal, such as annealed stainless steel. The pair of fingers and the circumferential shoulder may be configured such that increase distally directed force applied to the plunger member after the proximal drug chamber is completely collapsed will overcome the interference between the pair of fingers and the circumferential shoulder to allow distally directed motion of the proximal stopper member relative to the elongate fluid conveying member. The circumferential shoulder may have a larger diameter than other portions of the elongate fluid conveying member.

The aforementioned and other embodiments of the invention are described in the Detailed Description which follows.

BRIEF DESCRIPTION OF THE DRAWINGS

FIGS. 1A to 5C illustrate various aspects of conventional injection syringe configurations.

Figure 1A:
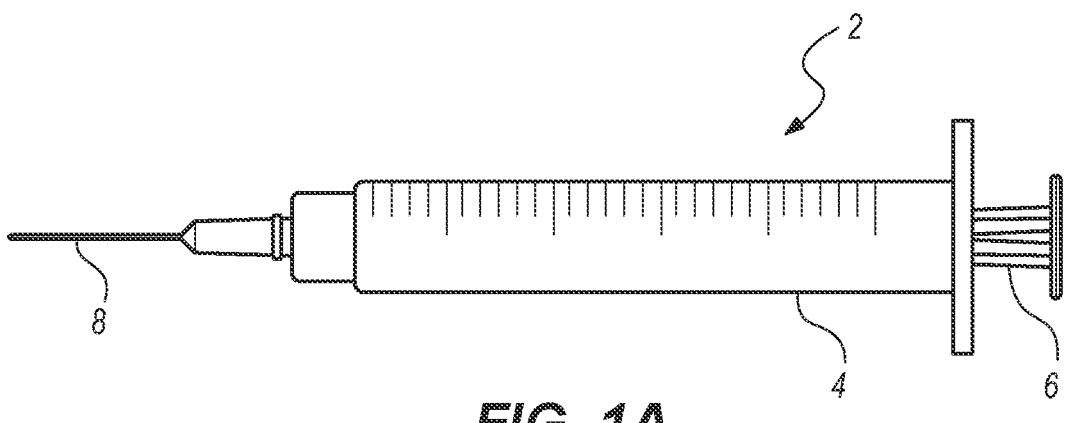
Figure 1B:
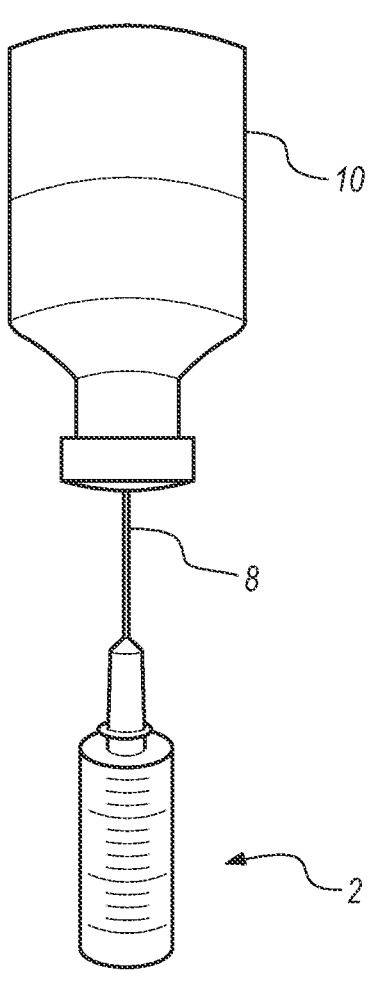
Figure 2A:
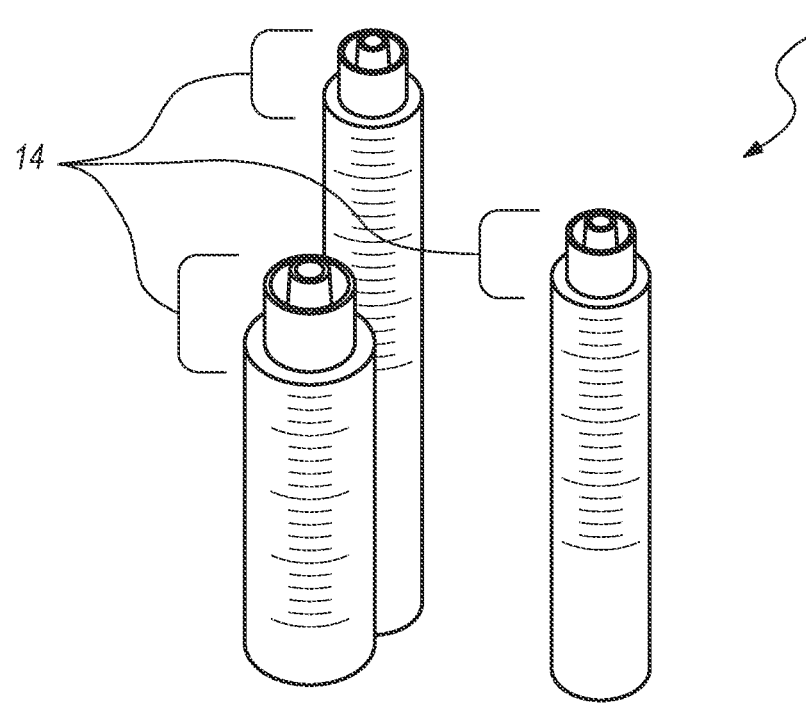
Figure 2B:
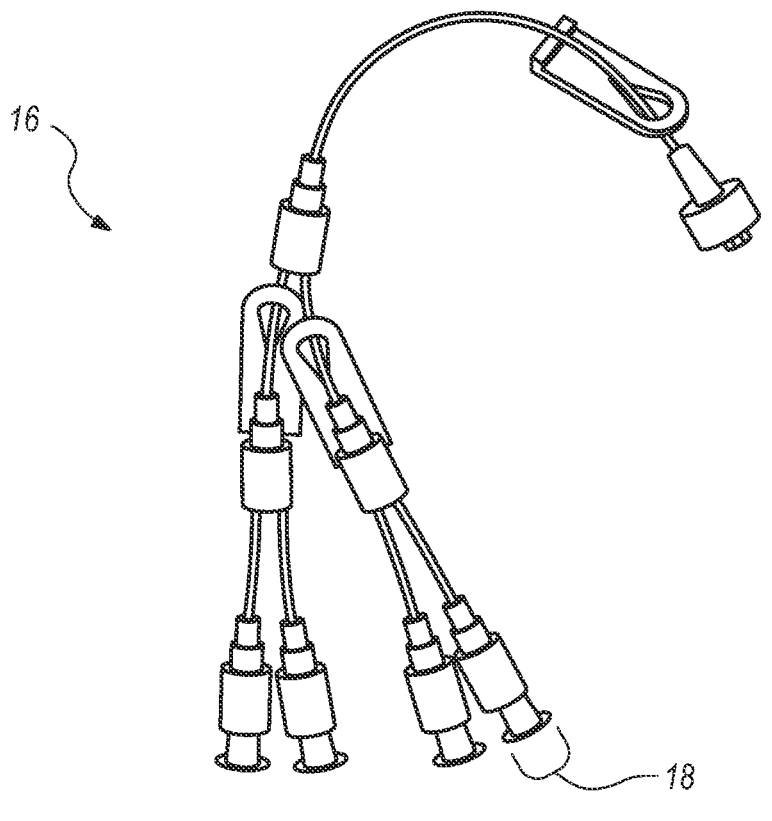
Figure 5A:
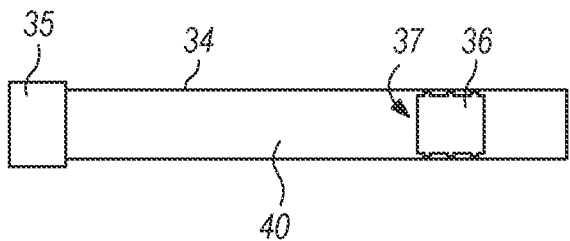
Figure 5B:
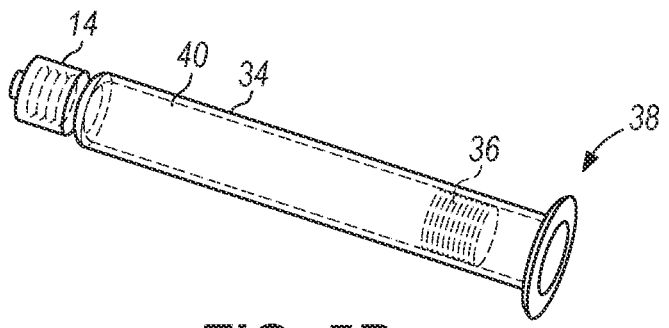
Figure 5C:
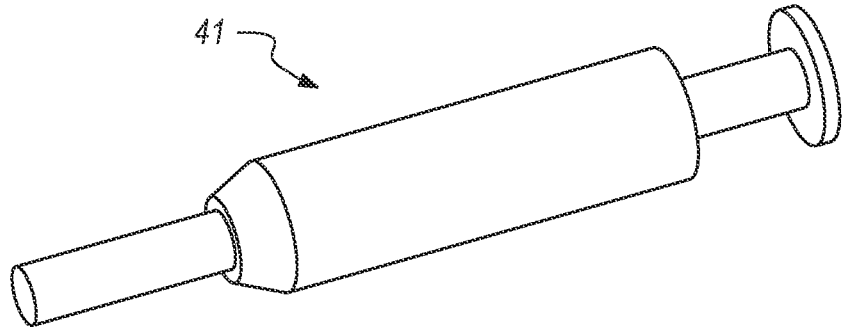

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Figures 6A, 6B:
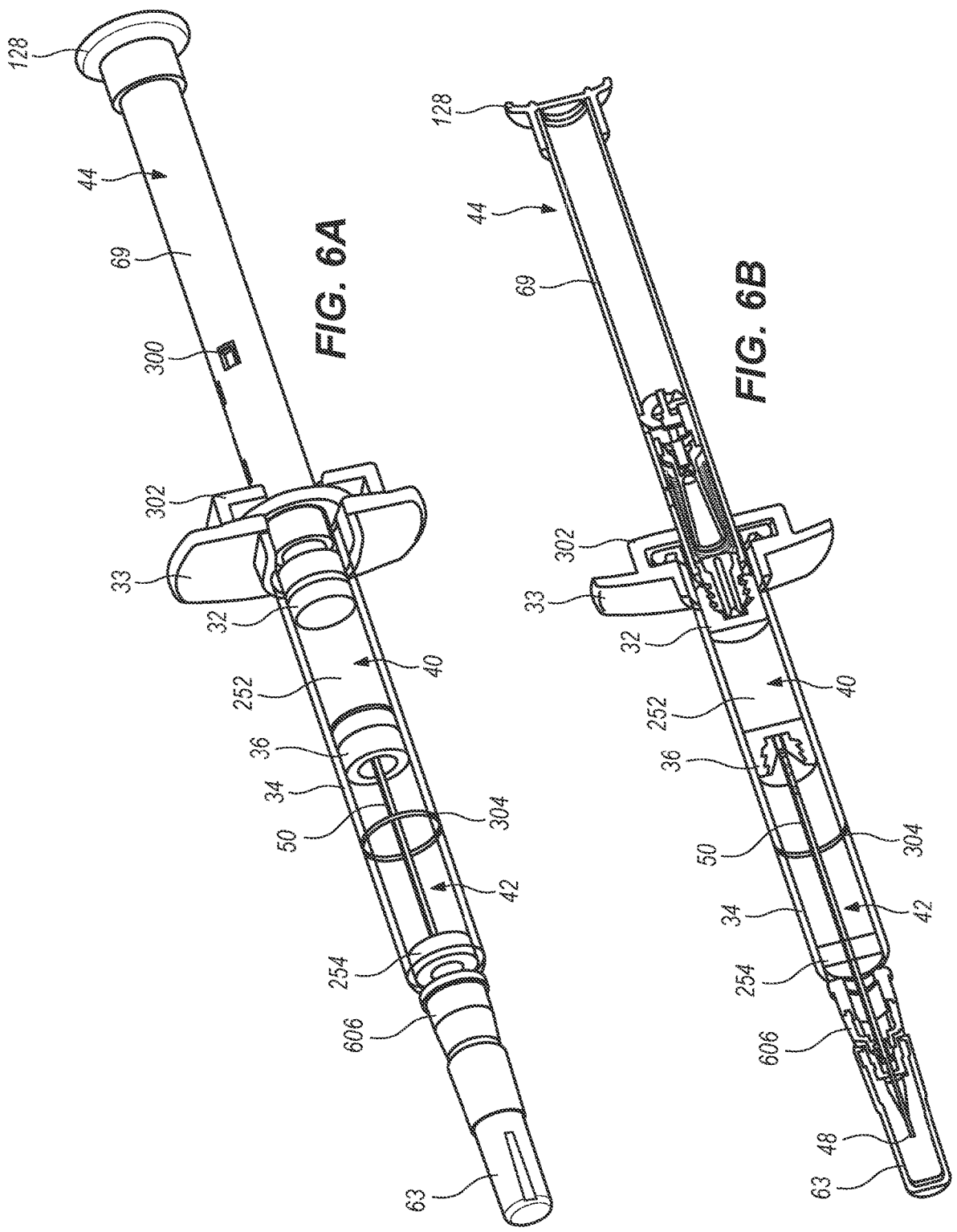
FIGS. 6A and 6B are perspective and longitudinal cross-section views illustrating various aspects of syringe based dual chamber safe injection systems wherein a distal needle end/tip may be withdrawn into a protected configuration after use according to some embodiments.

Exemplary Prefilled Dual Chamber Safe Injection Systems
Exemplary Dual Chamber Safe Syringe Systems Referring to FIGS. 6A-6B, a perspective and a longitudinal cross section view of a dual chamber safe injection system are shown, with a conventional off-the-shelf pre-filled syringe body (34) with conventional proximal and distal stopper members (32, 36) disposed therein. The proximal and distal stopper members (32, 36) together with the syringe body (34) define proximal and distal medicine chambers (40, 42). The proximal and distal stopper members (36, 37) occlude the proximal and distal ends of the proximal medicine chamber (40). The distal stopper member (36) occludes a proximal end of the distal medicine chamber (42). A needle coupling assembly (606) is disposed at the distal end of the distal medicine chamber (42) with a needle cover member (63) installed for storage. The dual chamber safe injection system controls transfer of a first medicine component from the proximal medicine chamber (40) to the distal medicine chamber (42) and exit of a mixed/combined medicine from the distal medicine chamber (42) distally subject to sequential insertion of a plunger member (44) relative to the syringe body (34) to various degrees by a user. The plunger member (44) includes the proximal stopper member (32), a plunger housing member (69) and a plunger manipulation interface (128). The first medicine component (252) located in the proximal medicine chamber (40) may be a liquid such as aqueous or oil based medicine solutions, a gel, or the first medicine component may be a diluent for mixing with the second medicine component (254) in the distal medicine chamber (42). The second medicine component (254) in the distal medicine chamber (42) may be a dry form medicine such as a powder, microspheres, emulsion, lyophilized or freeze dried medicine, or a cake like solid medicine.

The dual chamber safe injection system has a staked needle configuration wherein upon presentation to the user, a needle assembly, comprising a needle coupling assembly (606), a needle distal end/tip (48), a needle joining member, and a needle proximal end (50) are mounted in position ready for injection after removal of a needle cover member (63) which may comprise an elastomeric sealing material on its internal surface to interface with the needle distal end (48) or the distal housing portion (610) during storage. Alternatively, the needle cover member (63) may comprise a vent (not shown) for allowing pressure resulting from the transfer and mixing of the medicine components to escape from inside the syringe body (34) while preventing contamination from entering the syringe body (34). While, the staked needle is depicted as mounted in position, the staked needle may be removably coupled to the syringe body (34) using a Luer interface (not shown), with the proximal end (50) of the needle member extending through the Luer interface and into the distal medicine chamber (42). In the embodiments depicted in FIGS. 6A-7P, a significant portion of the safe needle retraction hardware resides within a plunger housing (69).

The dual chamber safe injection system (100) has a staked needle configuration wherein upon presentation to the user, a needle assembly, including a needle spine assembly ("needle") (76) and a needle coupling assembly (606) are mounted in position ready for injection after removal of a needle cover member (63) which may comprise an elastomeric sealing material on its internal surface to interface with a needle distal end (78) and/or a distal housing portion during storage. Alternatively, the needle cover member (63) may comprise a vent (not shown) for allowing pressure resulting from the transfer of the first medicine component/diluent (252) to escape from inside the syringe body (34) while preventing contamination from entering the syringe body (34). While, the staked needle is depicted as mounted in position, the staked needle may be removably coupled to the syringe body (34) using a Luer slip or a Luer lock interface (not shown), with the proximal end (50) of the needle member extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801,281, which was previously incorporated by reference herein. In the embodiments depicted in FIGS. 6A and 6B, a significant portion of the safe needle retraction hardware resides within a plunger housing (69).

Figures 7A, 7B:
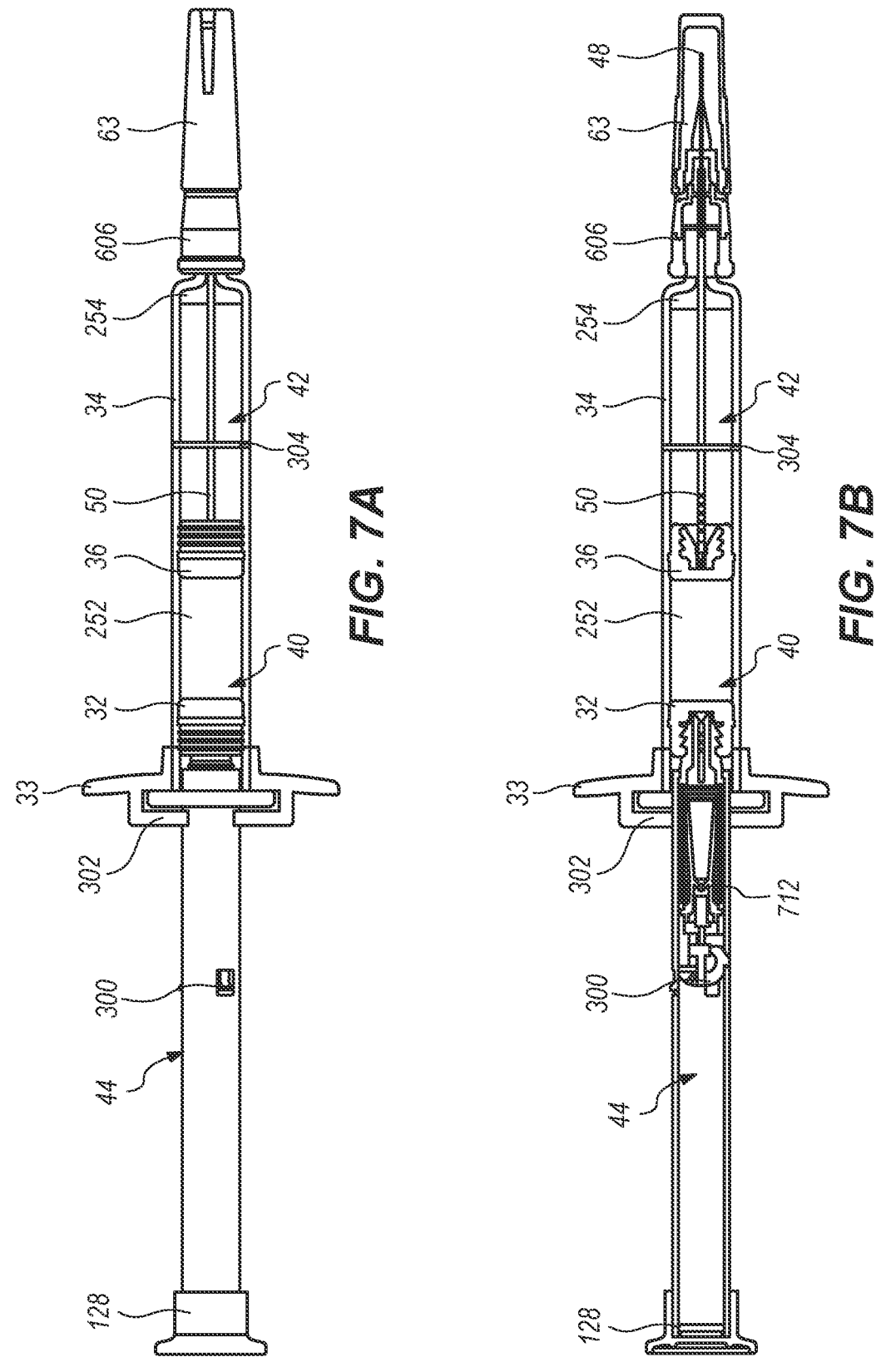
FIGS. 7A to 7P are side and longitudinal cross-section views illustrating various aspects of syringe based dual chamber safe injection systems during steps in methods for mixing and injecting using same according to some embodiments.
Figure 7C:
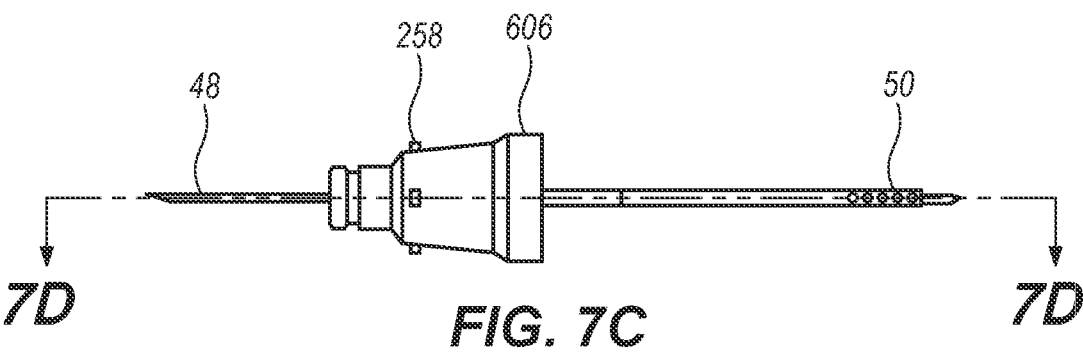
Figure 7D:
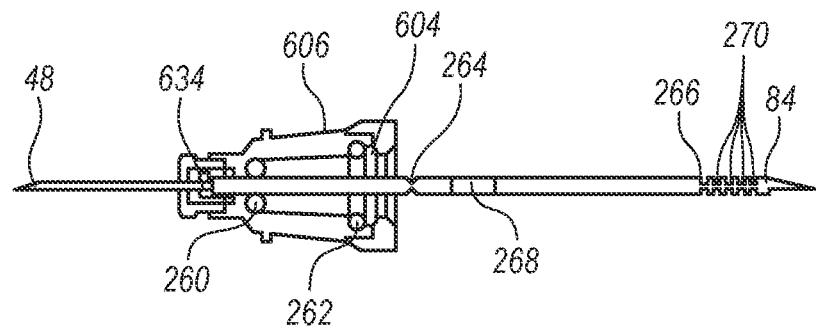
Figure 7E:
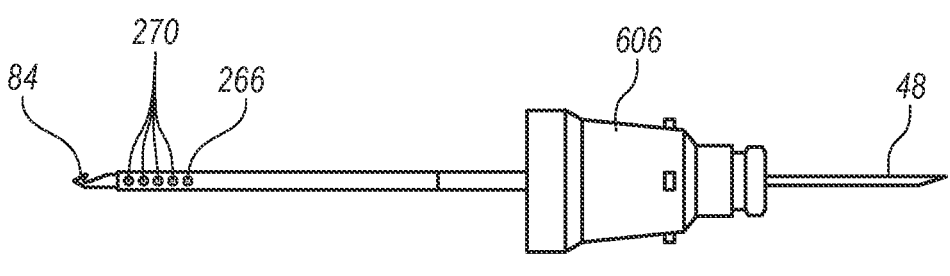
Figure 7F:
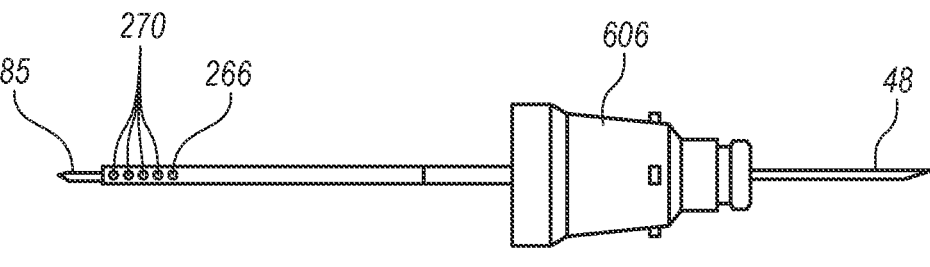
Figure 7G:
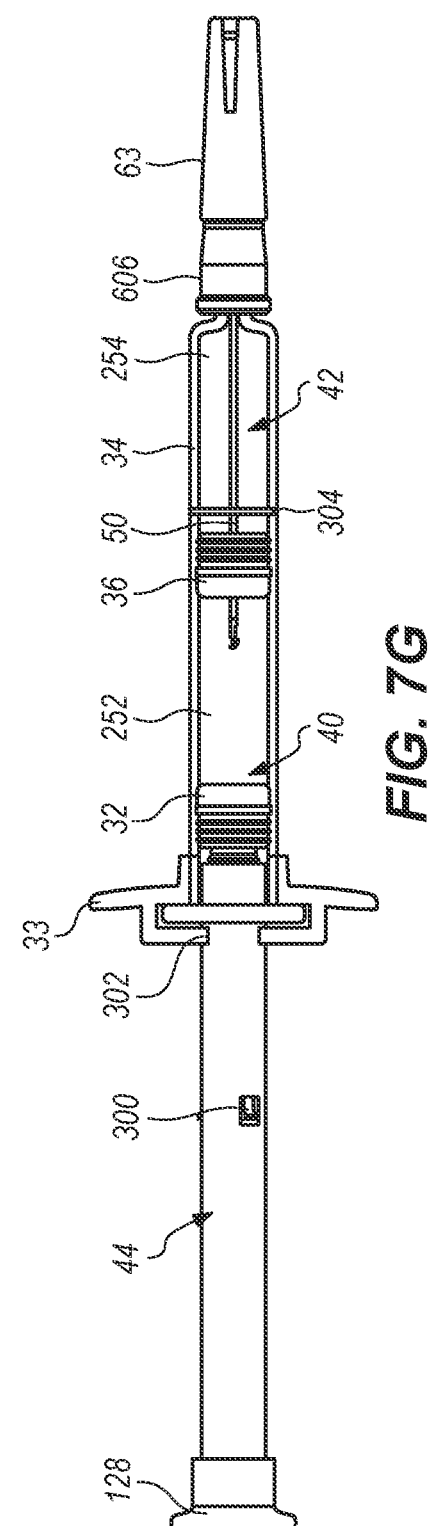
Figure 7H:
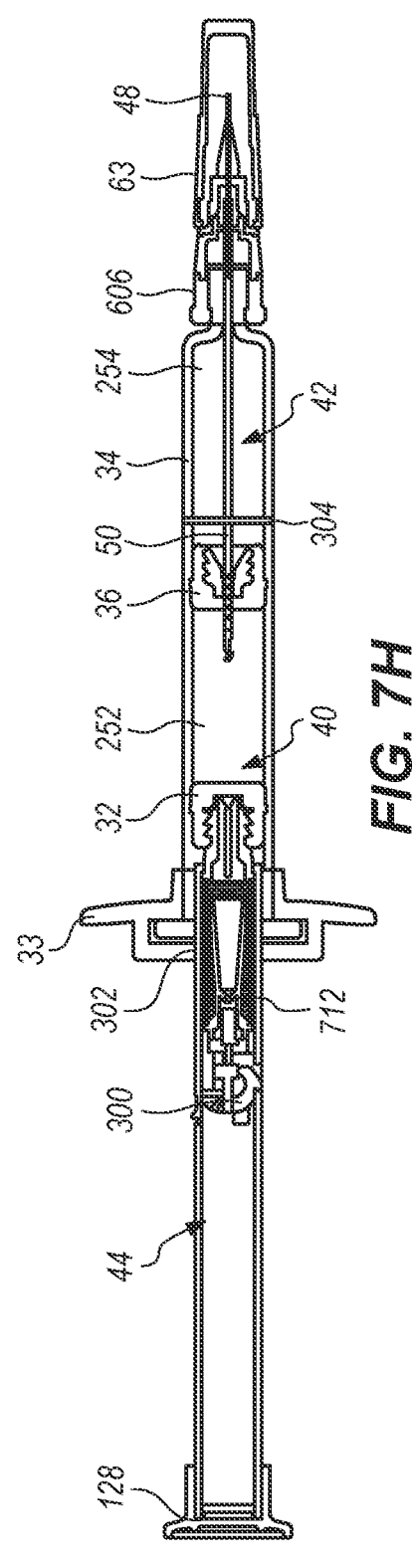
Figure 7I:
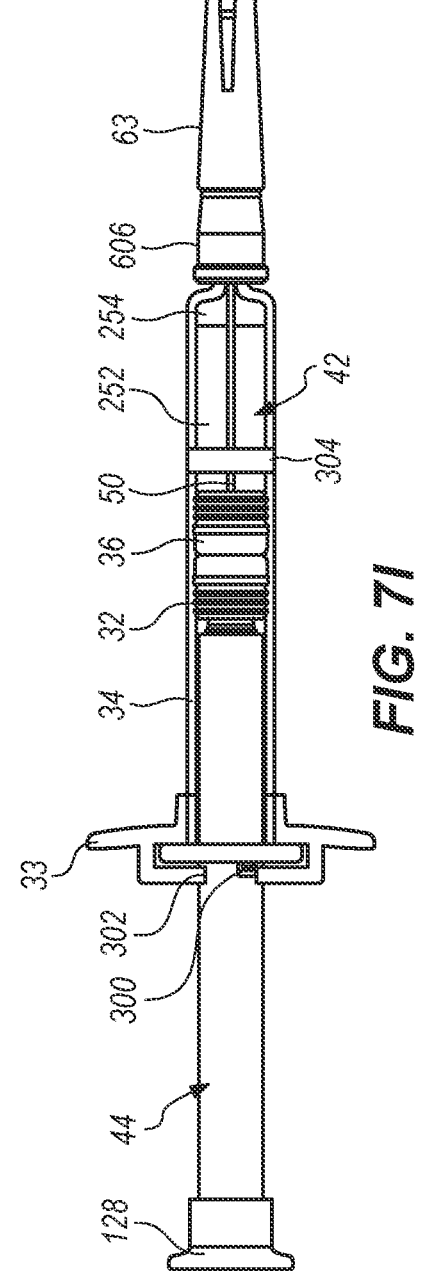
Figure 7J:
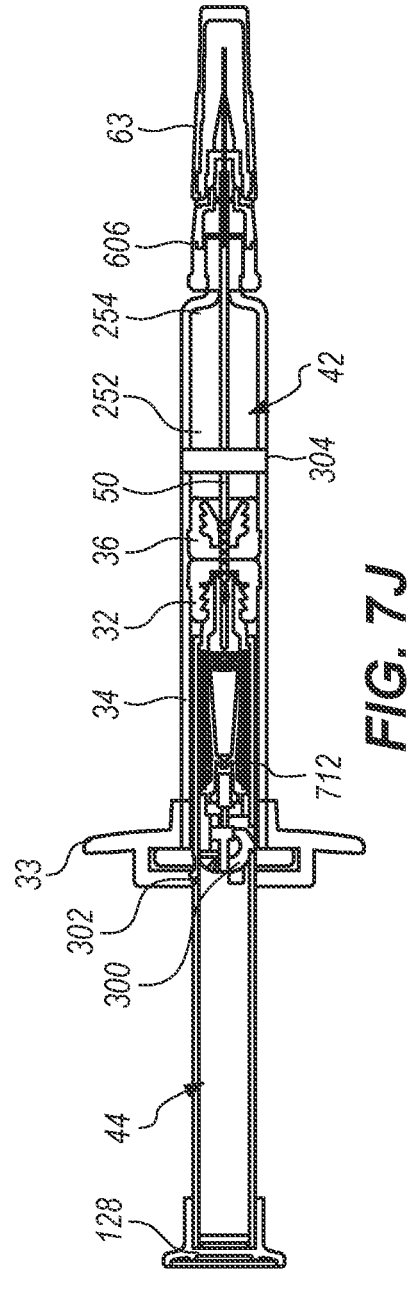
Figure 7K:
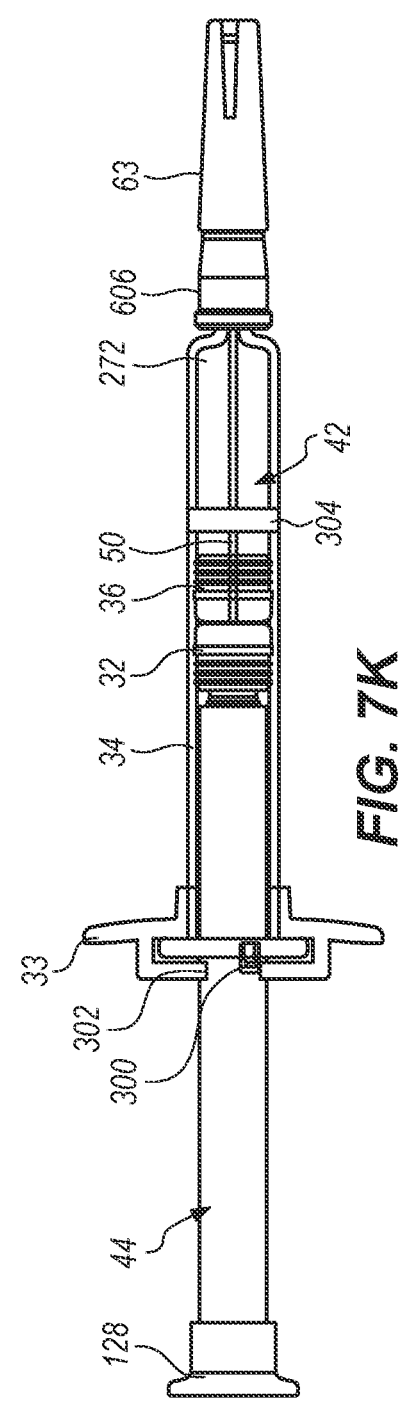
Figure 7L:
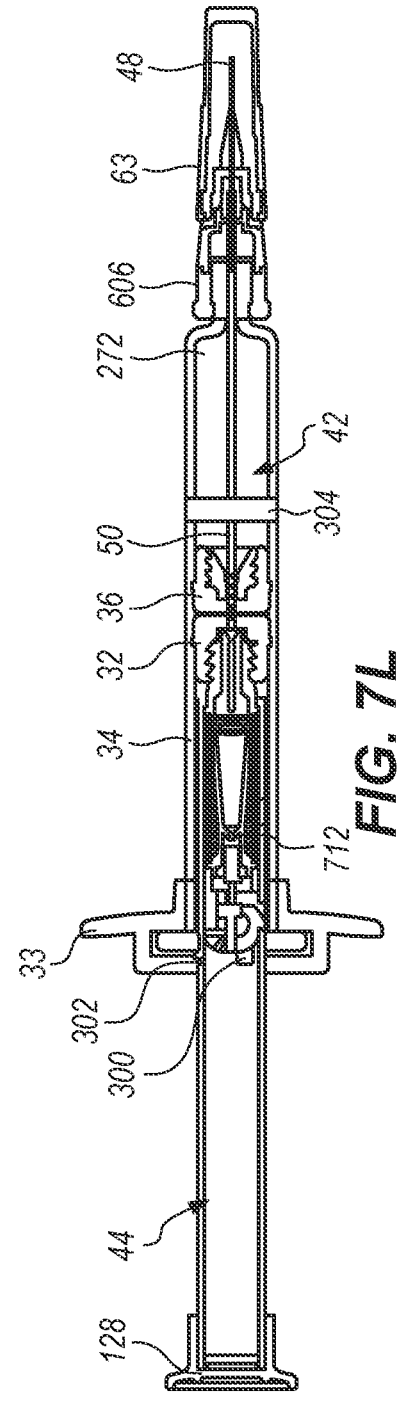
Figures 7M, 7N:
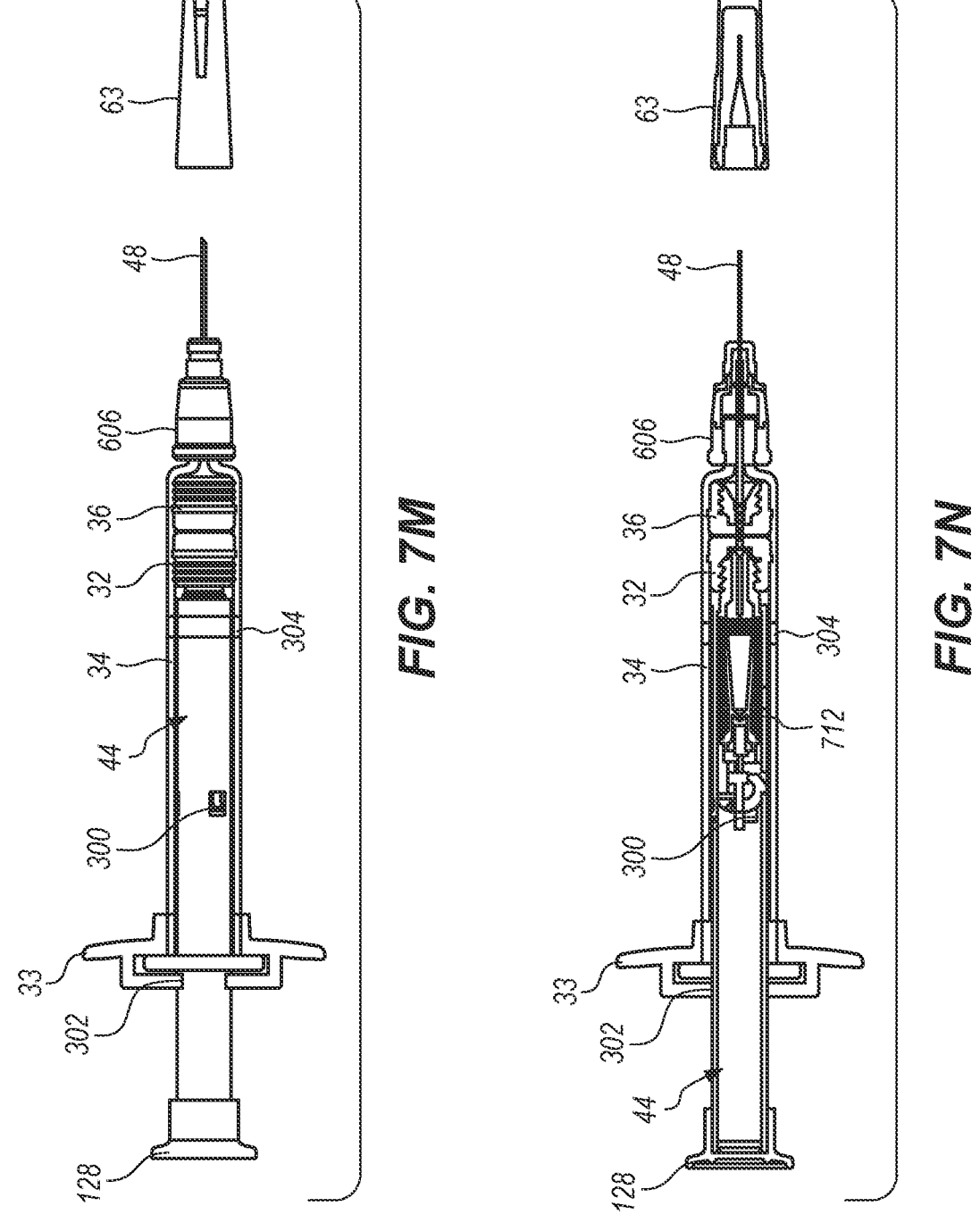
Figures 7O, 7P:
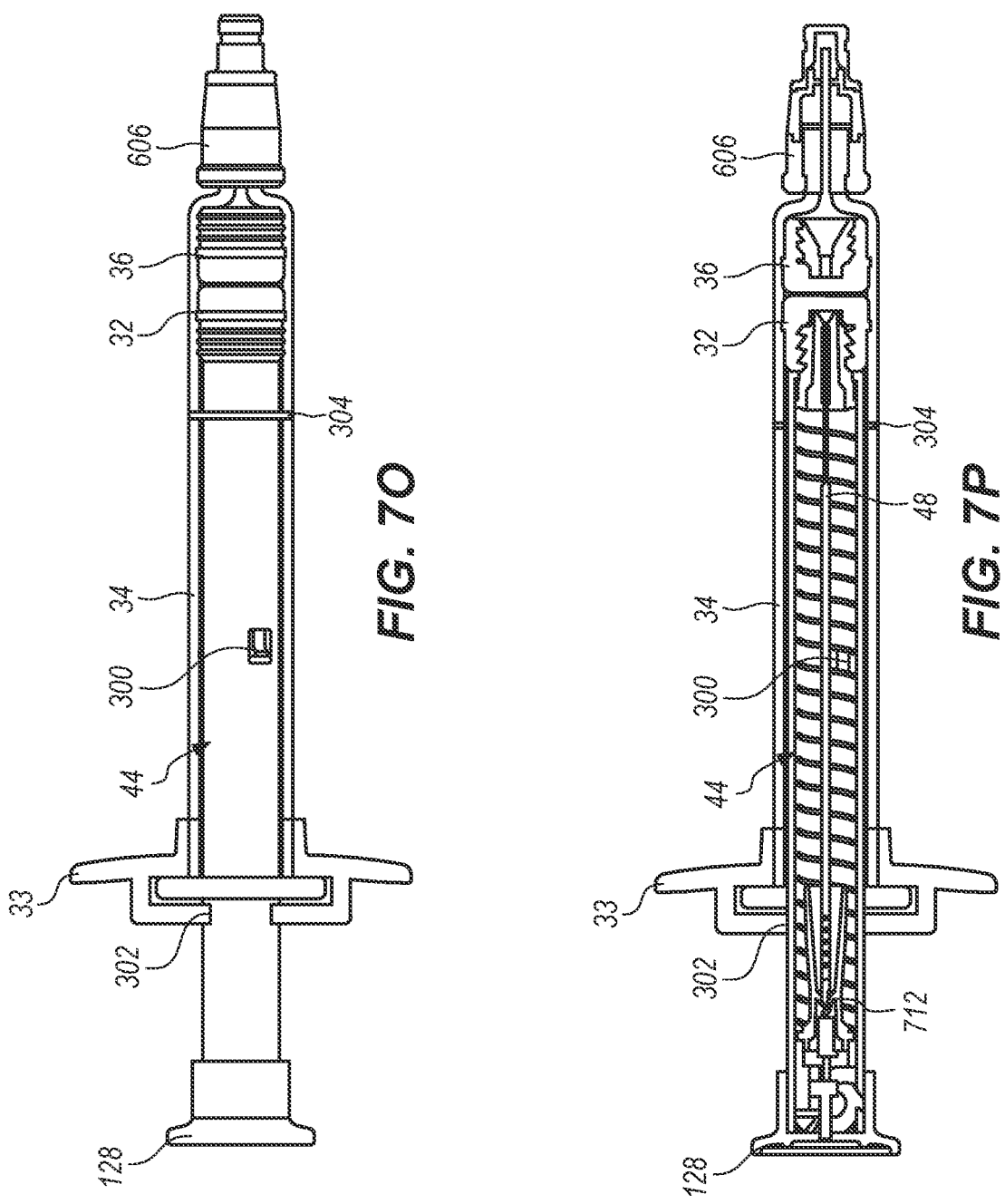

Referring to FIGS. 7A-7P, various aspects of configurations designed to facilitate injection of multi-part medications and retractions of a needle into a syringe body are illustrated, wherein two or more medication components are combined to form an injection combination or solution shortly before delivery into the patient. In one variation, a liquid first medicine component/diluent (252) may be combined with a substantially non-liquid second medicine component (254), such as a powdered form, of a drug agent, such as a freeze-dried or lyophilized drug component, shortly before injection. The configurations described herein in reference to FIGS. 7A-7P relate to dual-chamber configurations, wherein two or more chambers within the same syringe body (34) are utilized to carry, mix, and inject an injection solution.

Referring to FIGS. 7A and 7B, proximal and distal medicine chambers (40, 42) are formed by a distal stopper member (36) in between two portions of the interior of a syringe body (34), such that the distal medicine chamber (42) contains an air or gas gap, as well as a non-liquid medication (254); a proximal medicine chamber (40), on the opposite side of the distal stopper member (36) contains a liquid diluent (252), which is proximally contained by a proximal stopper member (32). The liquid diluent (252) is a first component of a medicine and the non-liquid medication (254) is a second component of the medicine.

Referring to FIG. 7C, and the associated cross sectional view in FIG. 7D, various components of a needle coupling assembly (here a so-called "staked" needle coupling assembly (606) is illustrated, but other needle assemblies as described below, including Luer-coupled as well as staked configurations, may be utilized). Lug features (258) are configured to assist with coupling the needle coupling assembly (606) to a needle cover member (63), as shown in FIG. 7A, for example. A small O-ring may be utilized as a sealing member (260) around the needle shaft, while a larger O-ring may be utilized as a sealing member (262) at the syringe body (34)/needle coupling assembly (606) interface. Alternatively, the small O-ring (260) and the large O-ring (262) may be combined into a single seal that performs both of the O-ring sealing functions. Also, the small O-ring (260) may be used to seal both around the needle shaft and to the syringe body (34).

The needle includes a plurality (e.g., four) of proximal openings/ports (270) configured to allow for entry of a liquid diluent, to be expelled out of a more distally-located middle opening/aperture (266); a lumen plug (268) occludes the needle lumen to create the flow path from the proximal openings (270) to the middle opening (266) under conditions such as those described above in reference to FIGS. 6N and 7H. The needle also includes a distal opening (264) on the opposite side of the lumen plug (268) from the middle opening (266). The distal opening (264) is fluidly coupled to the needle distal end (48) through the needle to inject liquid into a patient.

Referring to FIG. 7E, a proximal harpoon interface (84) is configured to serially penetrate proximal and distal stopper members (32, 36), and couple with a coupling feature (such as a needle retention feature are illustrated, for example, in FIGS. 7N and 7P, element (712)) in the plunger member (44). FIG. 7F illustrates a spike style harpoon coupling interface (85) that is configured to serially pierce both proximal and distal stopper members (32, 36) and couple with a coupling feature in the plunger member (44) to retract the needle member at least partially into the plunger member (44) after the injection has been given to the patient.

FIGS. 7A, 7B, and 7G-7P illustrate a sequence of actions for an injection procedure utilizing a dual chamber safe injection system such as that described above. Referring to FIGS. 7A and 7B, an injection assembly is in a stable configuration wherein it may be shipped or brought to an injection patient care scenario; a first drug component/liquid diluent (252) is isolated from a second non-liquid drug component (254), both within a syringe body on opposite sides of a distal stopper member (36).

FIGS. 7G and 7H illustrate initial insertion movement of the plunger member (44), advancing the distal (36) and proximal (32) stopper members together relative to the syringe body (34). Referring to FIG. 7H, with advancement sufficient to stab the proximal end (50) of the needle assembly across the distal stopper member (36), a fluid pathway is formed between the two previously isolated chambers (40, 42) of the syringe body (34), such that the liquid first drug component (252) in the proximal medicine chamber (40) may flow into at least one of the proximal openings (270), through the transfer pipe (46), and exit the more distal middle opening (266), to reach the non-liquid second drug component (254) in the distal medicine chamber (42).

FIGS. 7I and 7J illustrate that with further insertion until the stopper members (36, 32) are immediately adjacent each other, the liquid first drug component/diluent (252) has moved into the distal medicine chamber (42) to join the non-liquid second drug component (254). FIGS. 7K and 7L illustrate that with time and/or manual agitation, the liquid first drug component/diluent (252) and previously non-liquid second drug component (254) become mixed to form a mixed medication solution (272).

In some embodiment, especially with lyophilized non-liquid second drug components, the mixed medication solution (272) may be formed with minimal or no agitation or time passage. In another embodiment, especially with drugs which are held in suspension or emulsified drugs, vigorous shaking may be necessary to facilitate mixing. In the case of vigorous shaking it is useful to the user to be able to remove their thumb from the plunger manipulation interface (128). During transfer of liquid first medicine component (252) from the proximal to the distal medicine chambers (40, 42) pressure may build up in the distal medicine chamber (42). This pressure acts upon the proximal and distal stopper members (32, 36) to resist stopper motion. The pressure buildup may also move the stopper members (32, 36) and plunger manipulation interface (128) proximally if the user does not have their thumb restraining the plunger member (44). Mixed configuration latches or "mix clicks" in the plunger member (44) (described in U.S. Utility patent application Ser. No. 15/801,259, which was previously incorporated by reference herein) may be utilized to provide resistance to plunger manipulation interface (128) motion due to pressure buildup and allow the user to release their thumb from the plunger manipulation interface (128) for shaking or mixing of the drug. The mix clicks may also provide an audible and/or tactile indication that the transfer of liquid first medicine component (252) has been completed. The distal medicine chamber (42) may also include an agitation device, which assists in mixing of the medicine components.

With the assembly ready for injection of the mixed solution (272), the needle cover member (63) may be removed and the patient may be injected with the exposed needle distal end (48) with depression/insertion of the plunger member (44) and associated stopper members (36, 32) as shown in FIGS. 7M and 7N. Referring to FIGS. 7O and 7P, with full depression/insertion of the plunger member (44) and associated stopper members (32, 36), the sharp needle distal end/point (48) may automatically retract at least partially through the distal and proximal stopper members (36, 32) to a safe position within either the syringe body (34), the needle coupling assembly (606), or at least partially within the plunger member (44). Automatic retraction of the needle at least partially within the plunger is described in U.S. utility patent application Ser. No. 14/696,342, which was previously incorporated by reference herein.

Further details regarding multiple chamber injection systems (components, methods using same, etc.) are disclosed in U.S. Utility patent application Ser. No. 15/801,259, and U.S. Provisional Patent Application Ser. Nos. 62/682,381 and 62/729,880, which were all previously incorporated by reference herein.

Exemplary Dual Chamber Injection Systems with Filters

Figure 8:
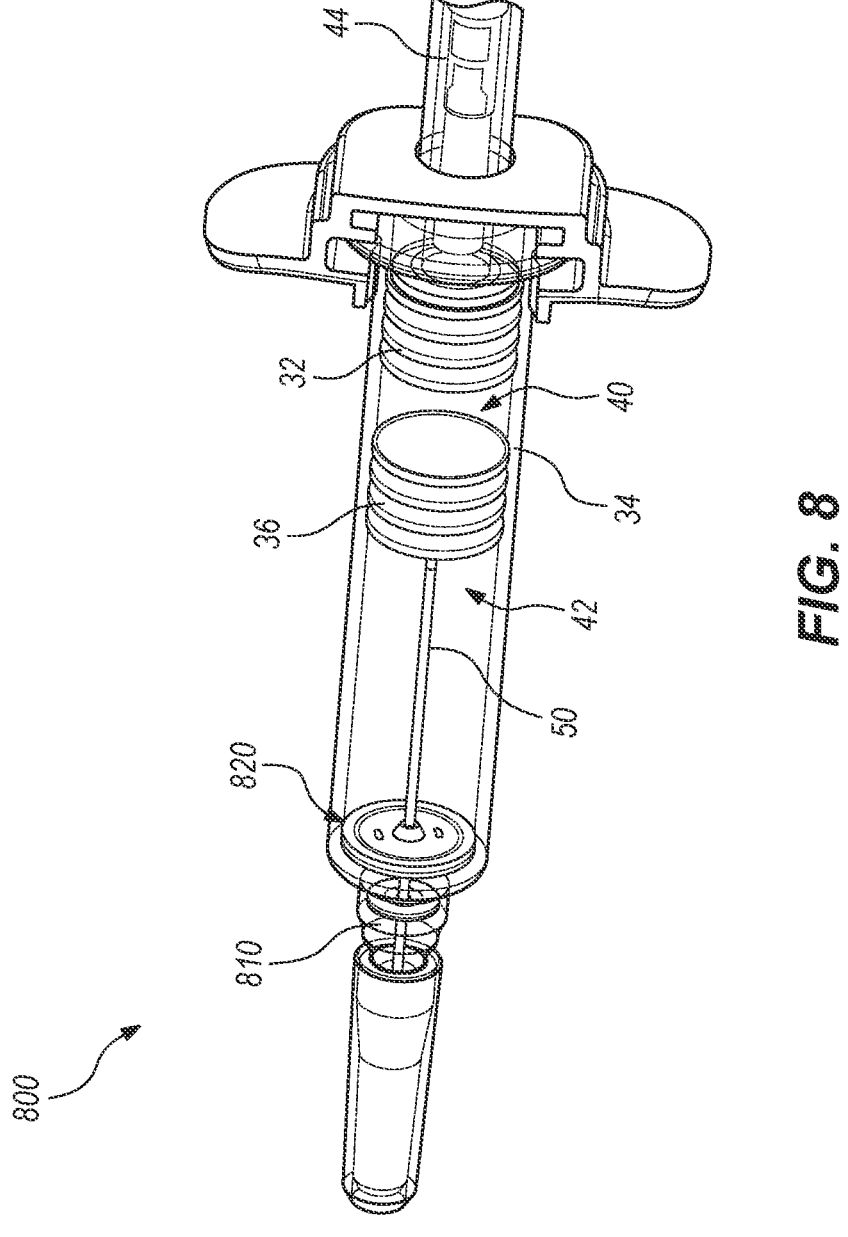
FIG. 8 is a perspective view illustrating various aspects of syringe based dual chamber injection systems according to some embodiments.

FIG. 8 depicts a dual chamber injection system (800) having a valve (820) disposed therein according to some embodiments. Similar to the dual chamber injection systems depicted in FIGS. 6A to 7P, the dual chamber injection system (800) includes an injection system body (34), proximal and distal stopper members (32, 36), a plunger member (44), and an elongate fluid conveying member (50). The proximal and distal stopper members (32, 36) together with the injection system body (34) form proximal and distal drug chambers (40, 42) as described herein. The proximal and distal drug chambers (40, 42) are prefilled with a liquid first medicine component and a non-liquid second medicine component (not shown for clarity; see 252, 254 in FIGS. 6A and 6B).

The injection system body (34) includes a distal needle interface (810) at a distal end thereof. In some embodiments, the distal needle interface (810) may be female Luer connector. The distal needle interface (810) may have many small spaces formed therein. If non-liquid second medicine component moves into some of the small spaces in the distal needle interface (810), the non-liquid second medicine component may clog these small spaces and prevent any liquid from exiting the injection system body (34). The non-liquid second medicine component in these small spaces may not dissolve, thereby changing the final concentration of medicines in the mixed medicine.

The valve (820) may perform one, two, three, or all of four functions described below. First, the valve (820) may minimize and/or eliminate movement of the non-liquid second medicine component into the distal needle interface (810) during assembly and storage of the injection system (800). Second, the valve (820) may center and stabilize the elongate fluid conveying member (50), thereby facilitating piercing of the distal stopper member (36) by the elongate fluid conveying member (50). Third, the valve (820) may minimize and/or eliminate drug loss during shaking mixing from a vented injection. Fourth, in vented injection systems (800) where the distal needle interface (810) is open to the atmosphere to allow the escape of air during liquid transfer from the proximal chamber (40) to the distal chamber (42), the valve (820) may prevent loss of the mixed medicine from the opening in the distal needle interface (810) during shaking and mixing of the medicine components. This fourth function prevents drug loss and protects the environment from toxic drugs. These valve functions, especially the third and fourth functions, facilitate the drug components in the proximal and distal chambers (40, 42) to be fully mixed before the mixed medicine is ejected distally out of the injection system body (34) through the distal needle interface (810) (e.g., into either a medication bag or a needle).

Figure 9:
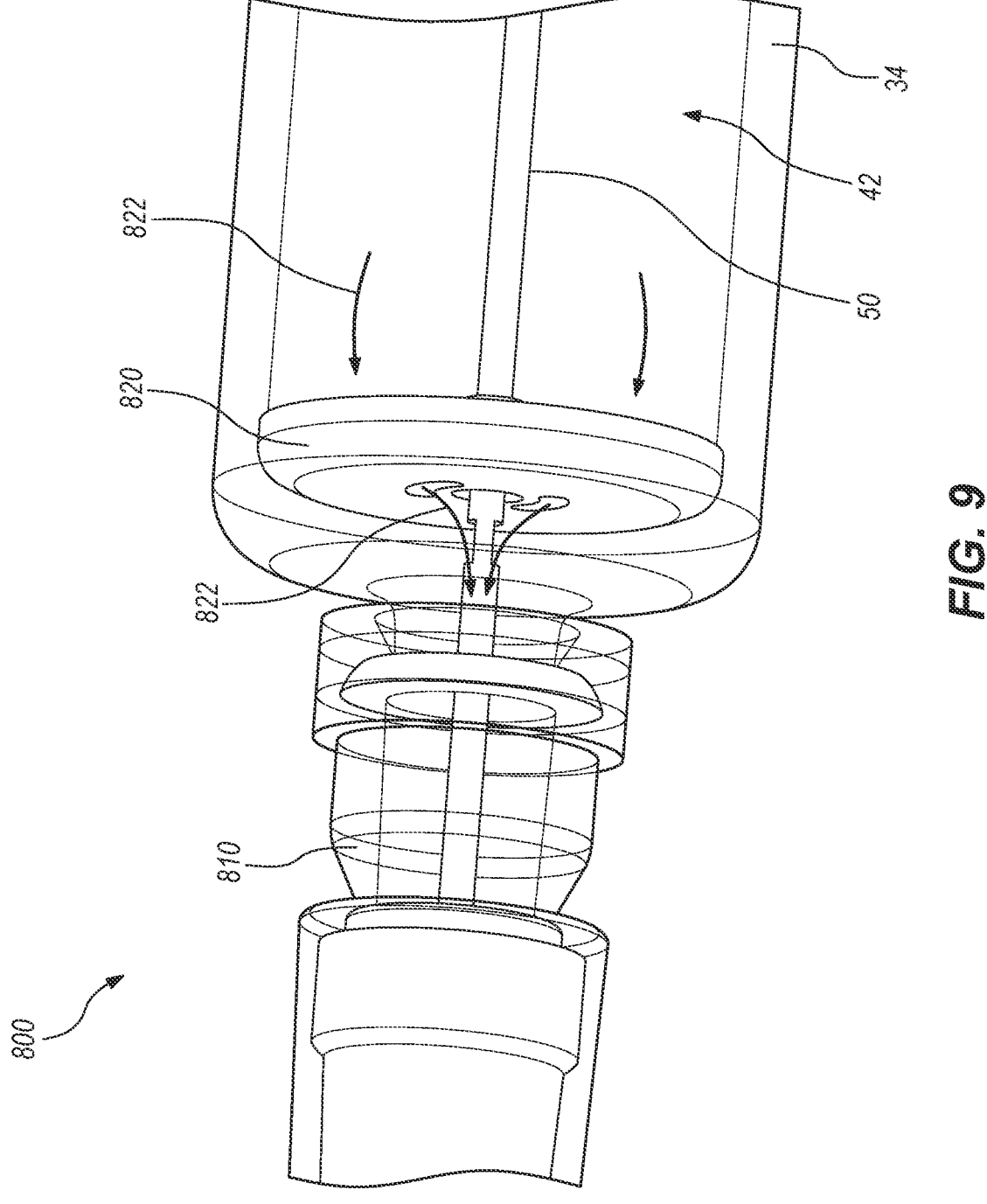
FIGS. 9 and 10 are detailed perspective views illustrating various aspects of syringe based dual chamber injection systems according to some embodiments.

As shown in FIG. 9, when the valve (820) is open after mixing and pressurizing the distal chamber (42), a fluid flow path (822) is available through the valve (820). The valve (820) may be configured to open after the proximal drug chamber (40) has been collapsed and the liquid first medicine component (252) has been transferred into the distal drug chamber (42) (see FIGS. 71 and 7J). At that time, the liquid first medicine component (252) and the non-liquid second medicine component (254) have been mixed, and the mixed medicine is ready to be ejected from the injection system body (34) for delivery to a patient.

Figure 10:
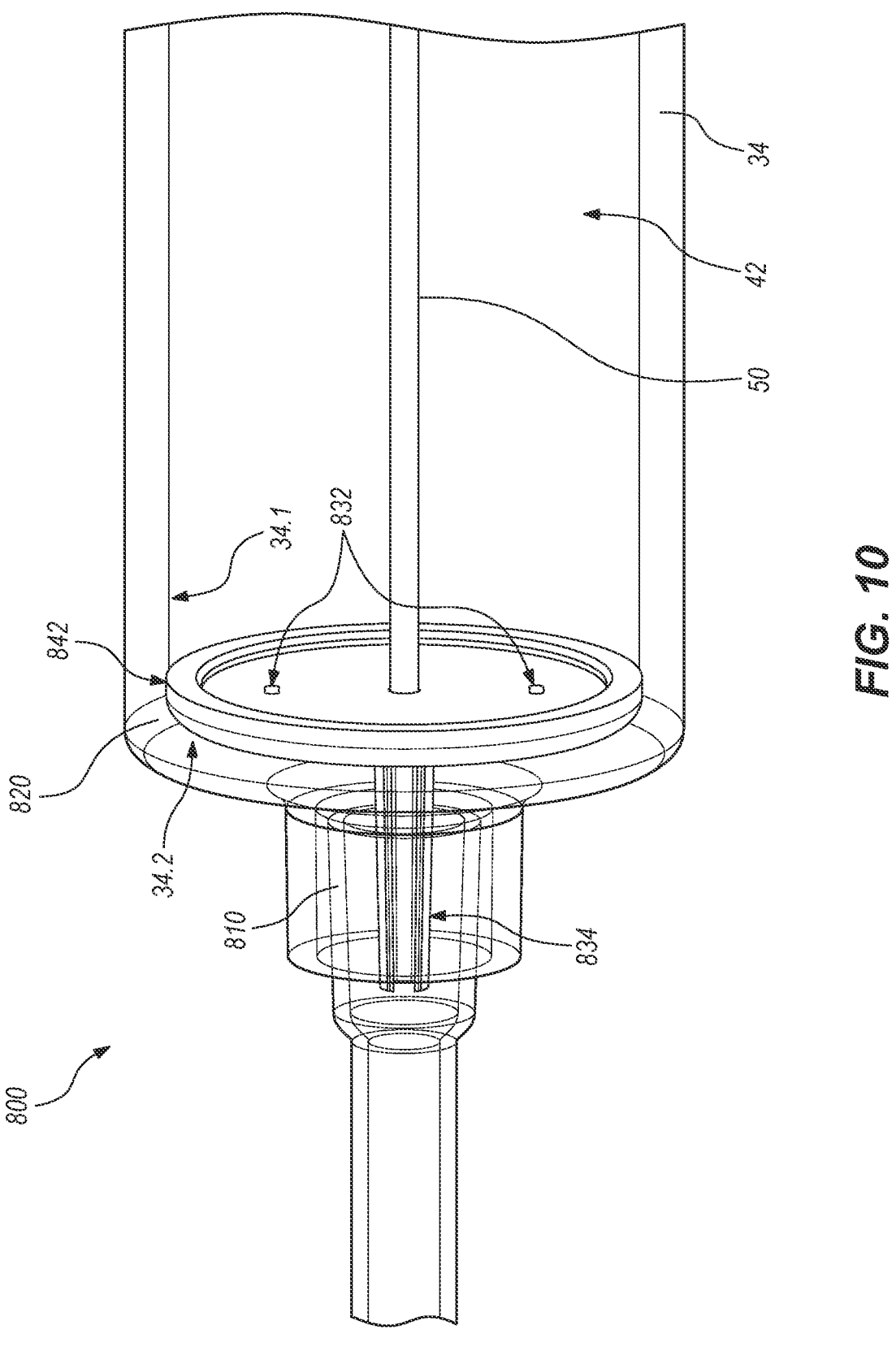

FIG. 10 depicts a dual chamber injection system (800) having a valve (820) disposed therein according to some embodiments in greater detail. The valve (820) defines a pair of ports (832) configured to be biased in a closed configuration to minimize and/or prevent the non-liquid second medicine component from passing therethrough. The ports (832) are also configured to change into an open configuration with increased pressure (e.g., greater than atmospheric pressure) in the distal drug chamber (42) to allow a liquid (e.g., the mixed medicine) to pass therethrough.

The valve (820) also defines a circumferential the gasket (842) configured to form a fluid tight seal with a circumferential inner surface (34.1) of the injection system body (34). The combination of the fluid tight seal from the gasket (842) and the closed configuration in which the pair of ports (832) are biased to minimize and/or prevent the non-liquid second medicine component from moving past the valve (820) into the distal needle interface (810).

In the embodiment depicted in FIG. 10, the valve (820) is restrained from moving distally relative to the injection system body (34) by interference with the distal end of the injection system body (34). The valve (820) also defines a distally extending member (834), which may be configured to center and/or stabilize the elongate fluid conveying member (50).

Figure 11:
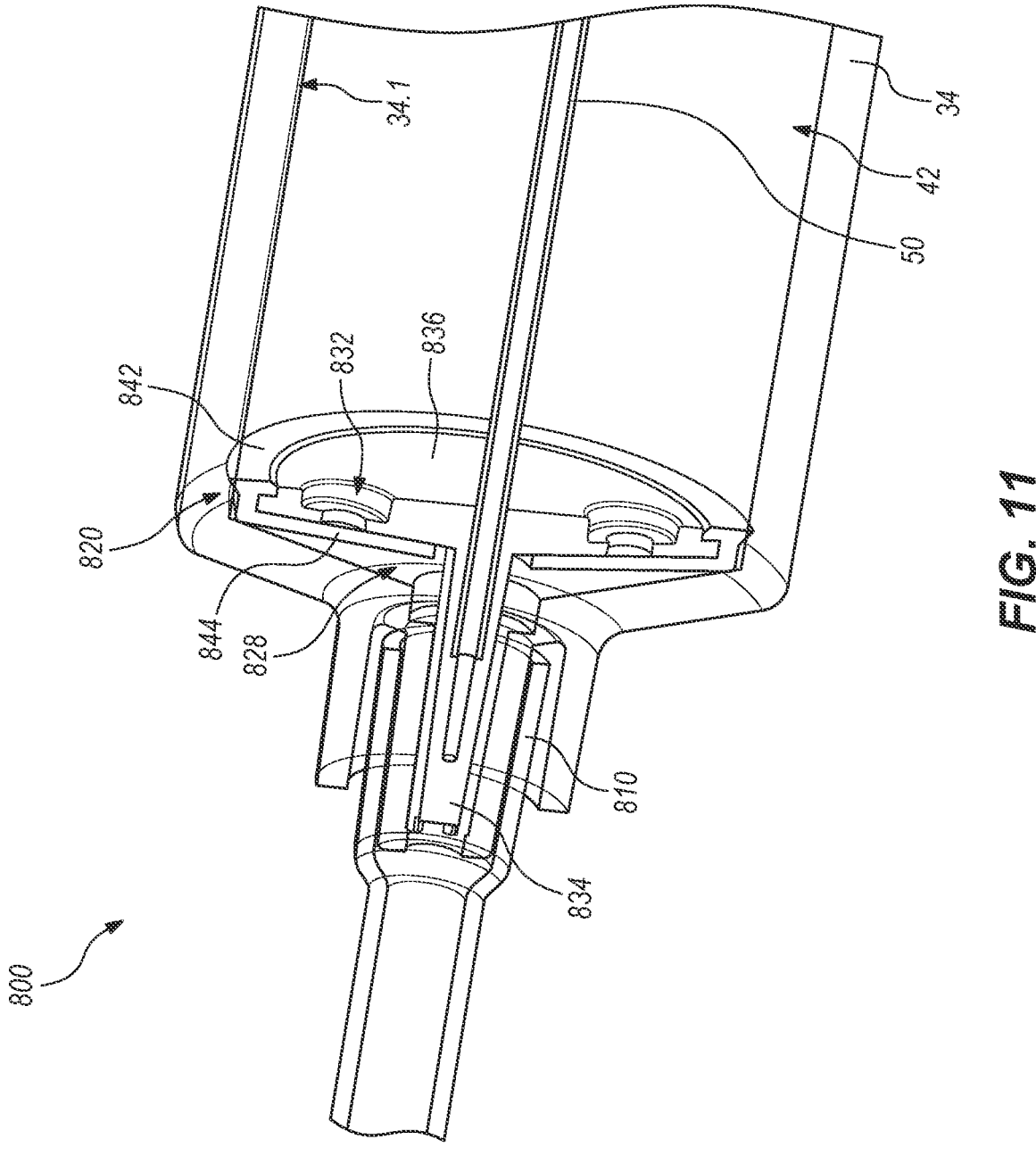
FIGS. 11 and 12 are detailed longitudinal cross-section views illustrating various aspects of syringe based dual chamber injection systems according to some embodiments.
Figure 13:
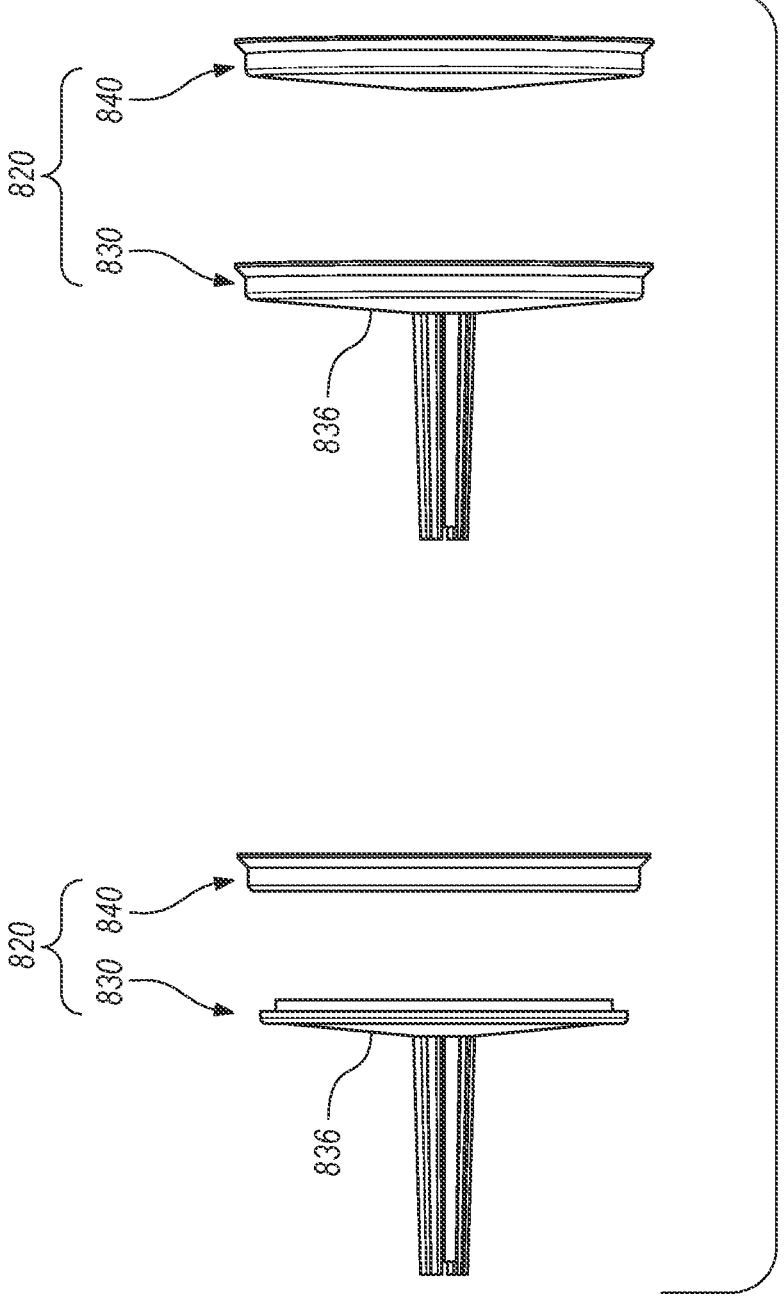
FIGS. 13 and 14 are exploded and perspective views of valves for use in dual chamber injection systems according to some embodiments.

FIG. 11 depicts a dual chamber injection system (800) having a valve (820) in a closed configuration disposed therein according to some embodiments in a detailed longitudinal cross-sectional view. The valve (820) includes a rigid member (830) and an elastic member (840) as shown in FIG. 13. The rigid member (830) may be made (e.g., molded) from cyclic olefin copolymer. The rigid member (830) defines a pair of ports (832), a distally extending member (834), and an annular portion (836).

The elastic member (840) may be made (e.g., molded) from a variety of elastic materials, such as rubber, thermoplastic elastomer, butyl rubber, or polyisoprene elastomer. The elastic member (840) defines a circumferential gasket (842) and an annular flap (844). The circumferential gasket (842) extends from the outer circumference of the annular flap (844) such that the elastic member (840) wraps around the annular portion (836) of the rigid member (830). The circumferential gasket (842) is configured to form a fluid tight seal with a circumferential inner surface (34.1) of the injection system body (34). The annular flap (844) in the elastic member (840) is biased to seal/close the pair of ports (832) in the rigid member (830).

The ports (832) are also configured to change into an open configuration with increased pressure (e.g., greater than atmospheric pressure) in the distal drug chamber (42) to allow a liquid (e.g., the mixed medicine) to pass therethrough.

The circumferential gasket (842) is also configured to exert a frictional force against the circumferential inner surface (34.1) of the injection system body (34) to couple the valve (820) to the injection system body (34). As such, interference between the distally extending member (834) of the rigid member (830) and the distal needle interface (810) is no longer needed to couple the valve (820) to the injection system body (34). The circumferential gasket (842) coupling the valve (820) to the injection system body (34) allows a greater range of tolerance in the distal needle interface (810) and the distally extending member (834). Further, in such embodiments, the valve (820) can align the distally extending member (834) approximately down the middle of the injection system body (34). The distally extending member (834) does prevent the valve (820) from moving too far distally in the injection system body (34), thereby providing a space (828) for the valve (820) to open as described herein.

Figure 12:
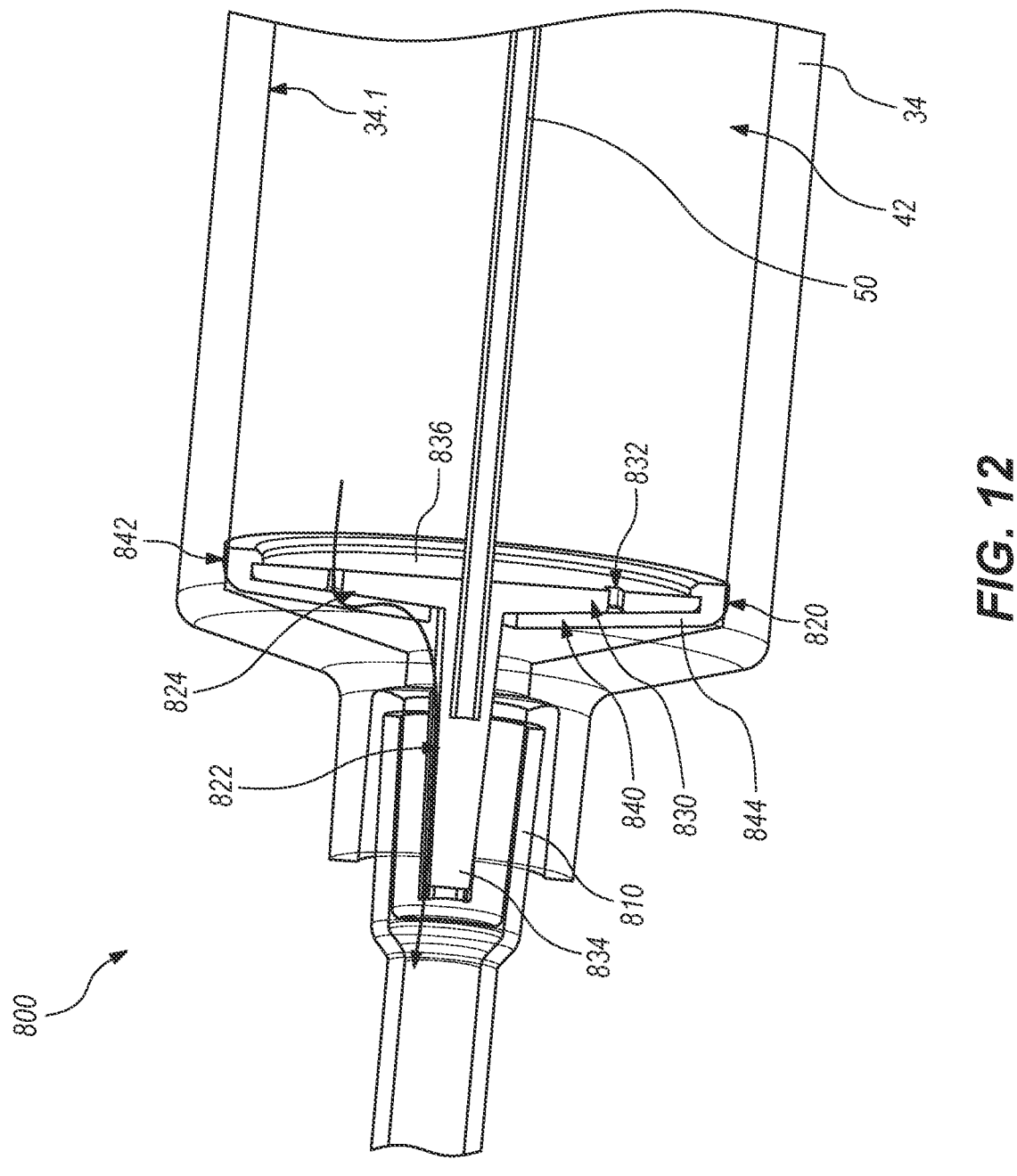

FIG. 12 depicts a dual chamber injection system (800) having a valve (820) in an open configuration disposed therein according to some embodiments in a detailed longitudinal cross-sectional view. The valve (820) is in an open configuration because of increased pressure (e.g., more than atmospheric pressure) in the distal drug chamber (42). The increased pressure pushes annular flap (844) away from the distal surface of the annular portion (836) of the rigid member (830). This opens a fluid flow path (822) through the valve (820). The fluid flow path (822) starts in the distal drug chamber (42), passes through at least one of the pair of ports (832), along a space (824) between the annular flap (844) and the annular portion (836) of the rigid member (830), and distally out a central opening (846) defined by the annular flap (844) in the elastic member (840). As such, increase pressure in the distal drug chamber (42) opens the space (824) between the annular flap (844) and the annular portion (836) of the rigid member (830) and the fluid flow path (822) through the valve (820).

The amount of pressure required to open the valve (820) can be adjusted/tuned by modifying various features of the valve (820), including but not limited to, the size of the ports (832), the contact force of the annular flap (844) over the ports (832), and the contact stress of the annular flap (844) against the ports (832). In the embodiment of the valve (820) depicted in FIG. 13, the annular portion (836) of the rigid member (830) forms a distally directed dome to increase the contact force and contact stress of the annular flap (844) over and against the ports (832).

Figure 14:
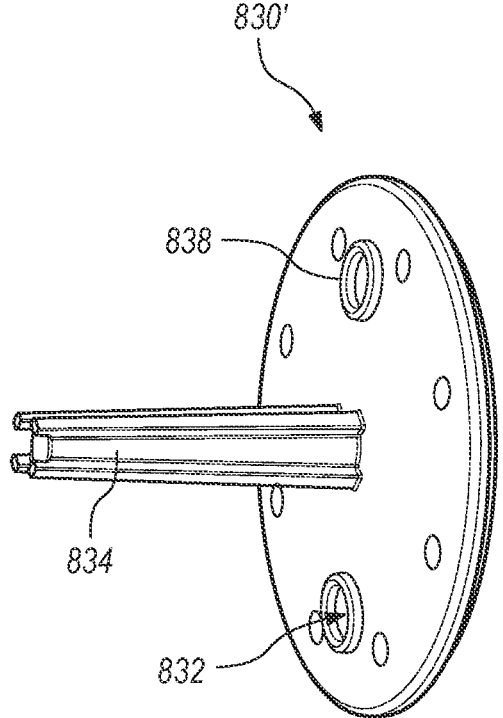

FIG. 14 depicts a rigid member (830') of a valve (820) according to some body. The rigid member (830') defines a raised annular wall (838) extending distally around each port (832). The raised annular wall (838) increases contact stress between the annular flap (844) and the sharp wall edge near the ports (832), thereby increasing the pressure required in the distal drug chamber (42) to open the valve (820).

Figure 15:
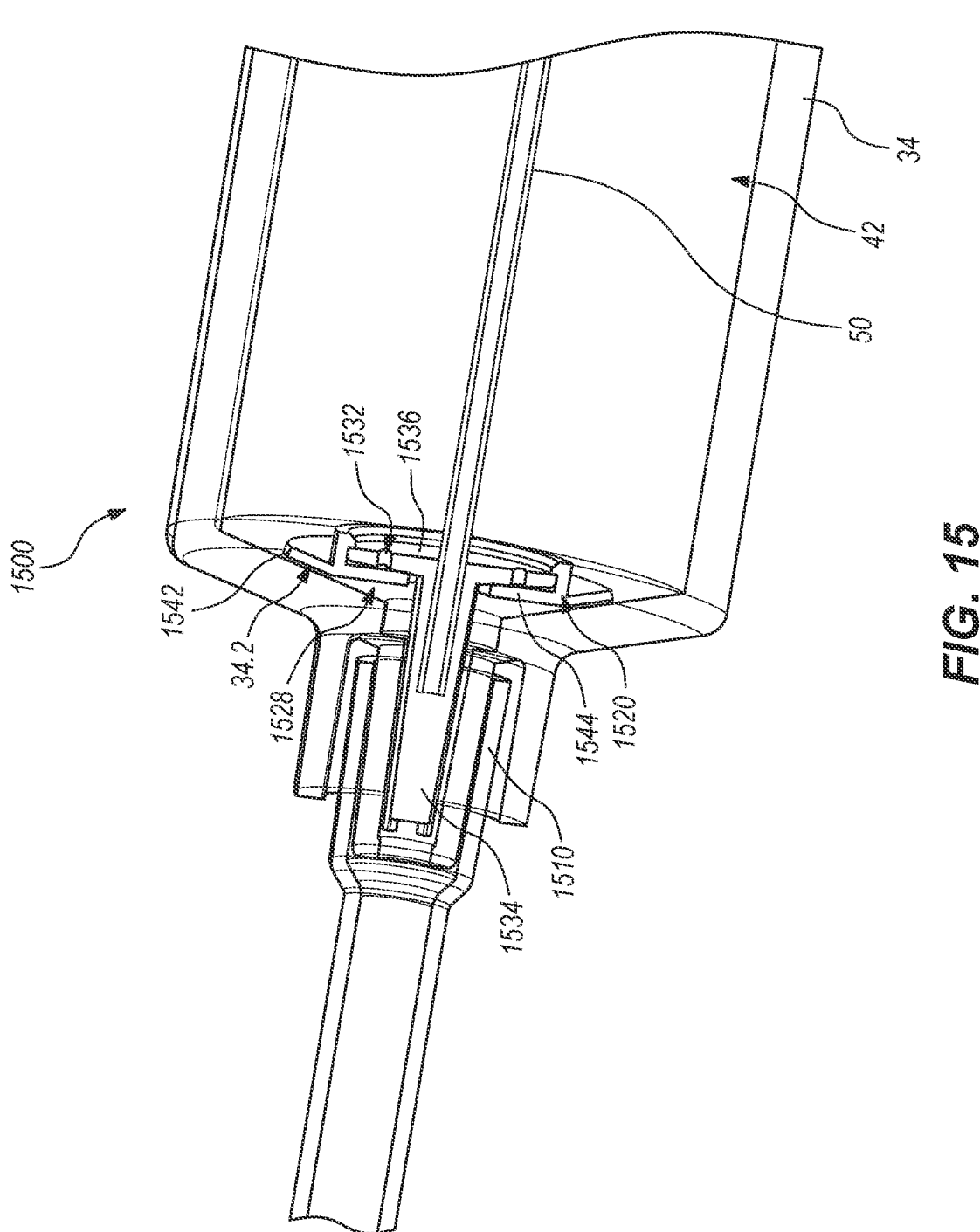
FIGS. 15 to 18 are detailed longitudinal cross-section views illustrating various aspects of syringe based dual chamber injection systems according to some embodiments.
Figure 16:
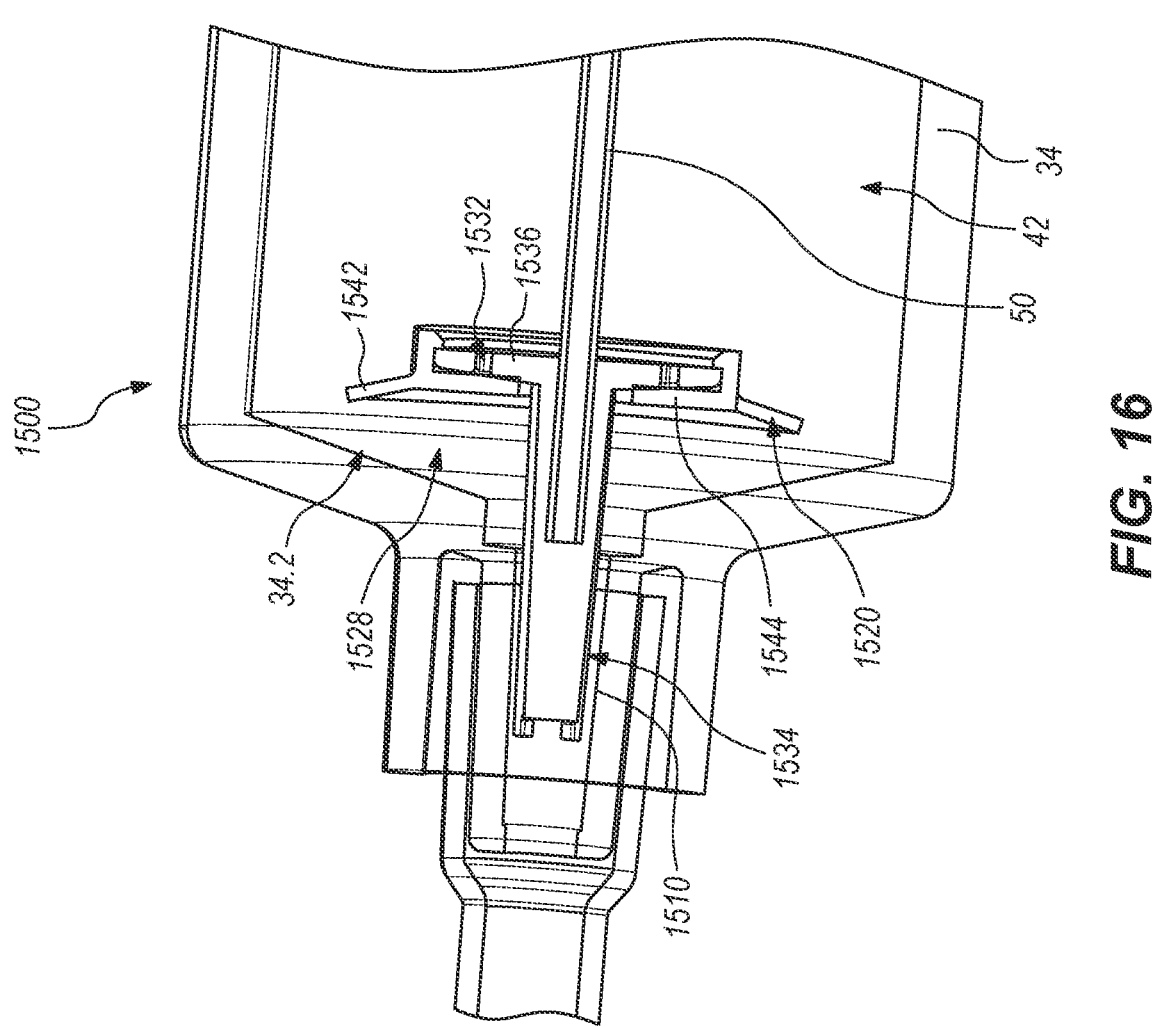
Figure 17:
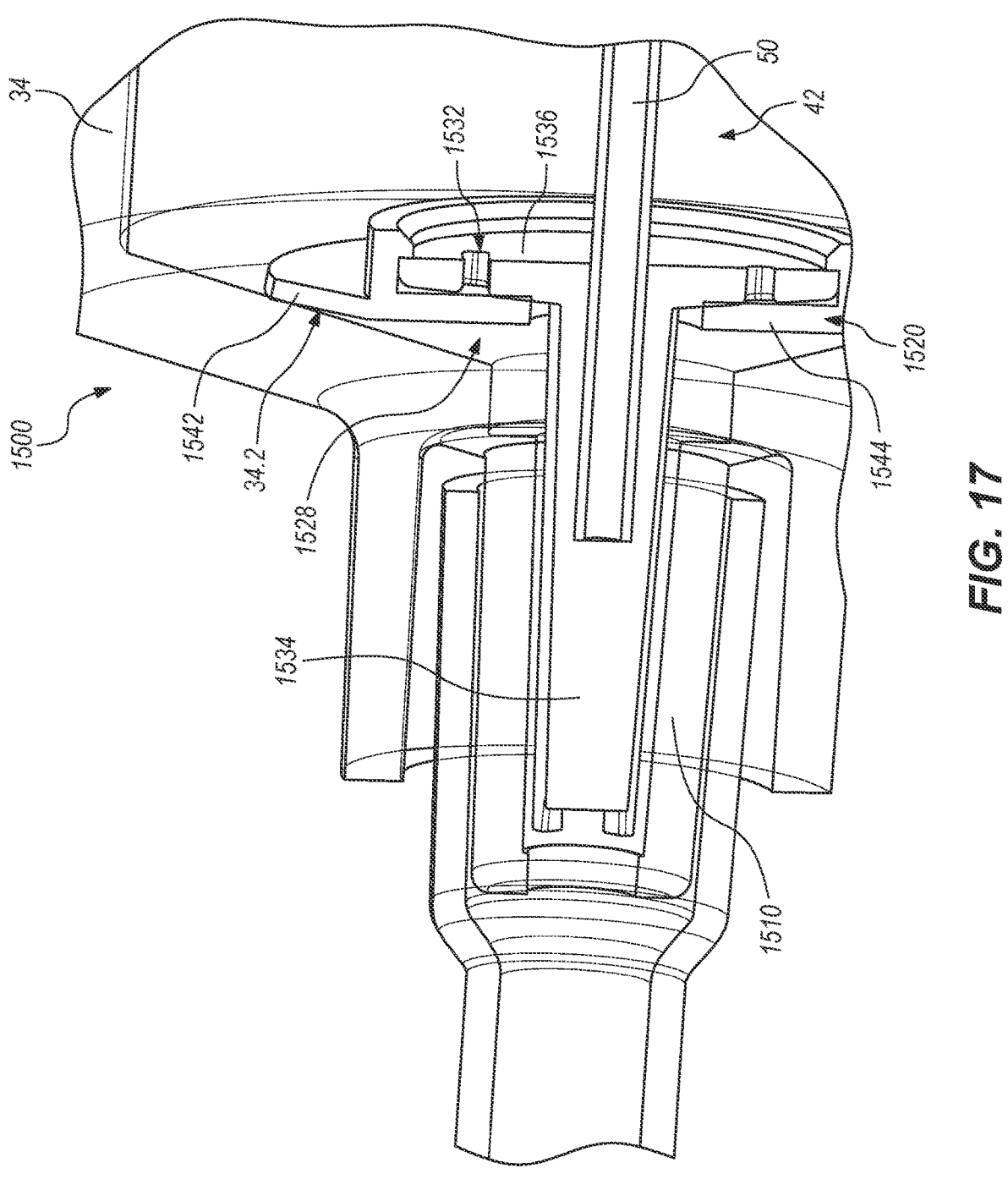

FIGS. 15 and 17 depict a dual chamber injection system (1500) having a valve (1520) in a closed configuration disposed therein according to some embodiments in a detailed longitudinal cross-sectional view. The valve (1520) includes a rigid member (1530) and an elastic member (1540). The rigid member (1530) defines a pair of ports (1532), a distally extending member (1534), and an annular portion (1536). FIG. 16 depicts the valve (1520) before it is completely inserted into the distal needle interface (1510) of the injection system body (34)

The elastic member (1540) defines a circumferential gasket (1542) and an annular flap (1544). The circumferential gasket (1542) extends from the outer circumference of the annular flap (1544) such that the elastic member (1540) wraps around the annular portion (1536) of the rigid member (1530). The circumferential gasket (1542) is configured to form a fluid tight seal with a distal inner surface (34.2) of the injection system body (34). The annular flap (1544) in the elastic member (1540) is biased to seal/close the pair of ports (1532) in the rigid member (1530).

The ports (1532) are also configured to change into an open configuration with increased pressure (e.g., greater than atmospheric pressure) in the distal drug chamber (42) to allow a liquid (e.g., the mixed medicine) to pass therethrough.

The distally extending member (1534) of the rigid member (1530) is configured to form an interference fit with the distal needle interface (1510) to couple the valve (1520) to the injection system body (34). Using the interference fit between the distally extending member (1534) and the distal needle interface (1510) to couple the valve (1520) to the injection system body (34) allows a single valve (1520) to be used with a plurality of injection system bodies having different diameters. Increased pressure (e.g., more than atmospheric pressure) in the distal drug chamber (42) pushes annular flap (1544) away from the distal surface of the annular portion (1536) of the rigid member (1530). This opens a fluid flow path (not shown) through the valve (1520) as shown in the related embodiments depicted in FIG. 12.

Figure 18:
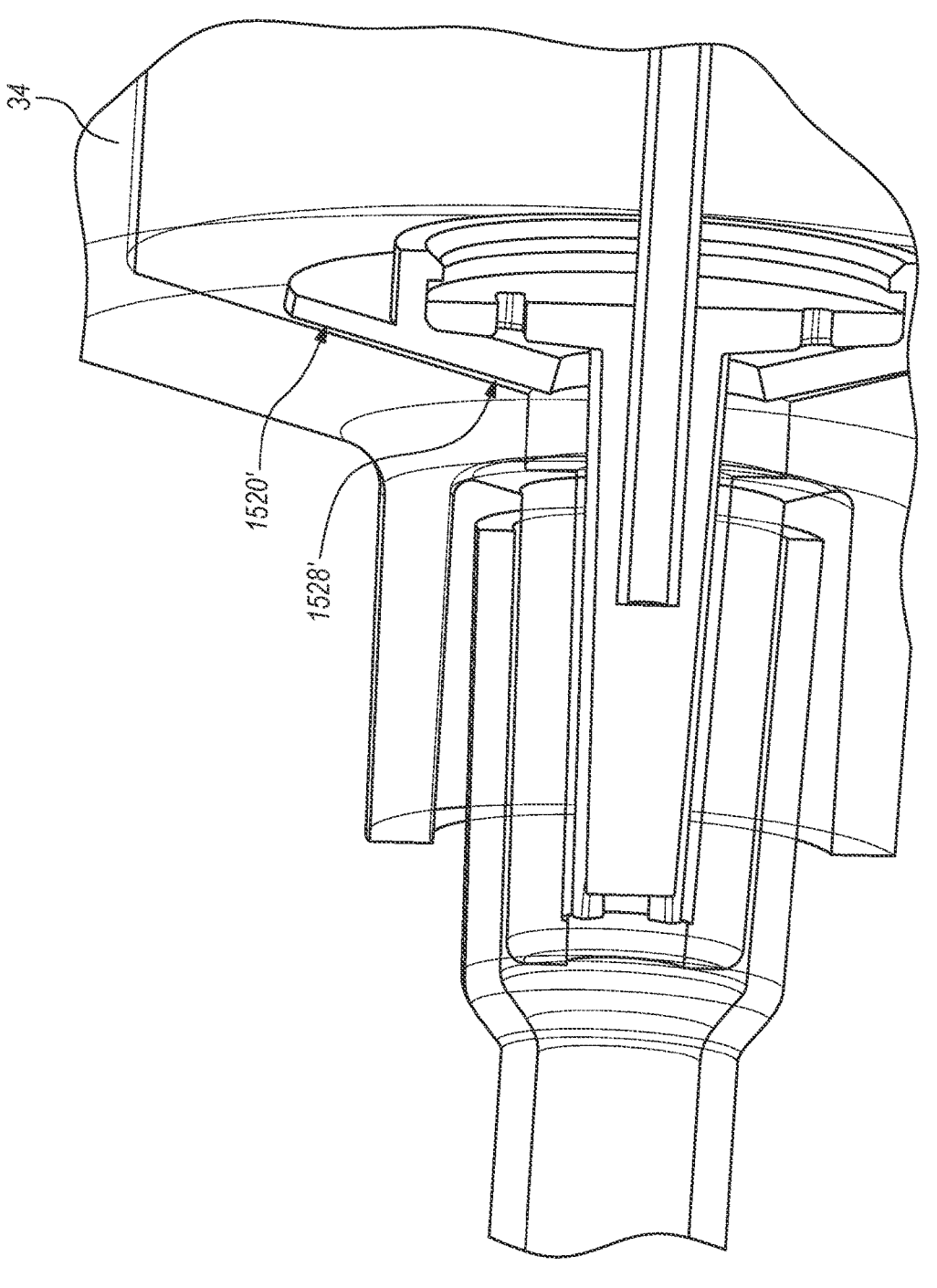

In the embodiment depicted in FIGS. 15 to 17, the interference fit between the distally extending member (1534) and the distal needle interface (1510) to couple the valve (1520) to the injection system body (34) precisely positions the valve (1520) relative to the injection system body (34). The distally extending member (1534) prevents the valve (1520) from moving too far distally in the injection system body (34), thereby providing a space (1528, see FIG. 17) for the valve (1520) to open as described herein. FIG. 18 shows a valve (1520') which has moved too far distally in the injection system body (34). As a result, the space (1528') is insufficient to allow the valve (1520') to open.

Figure 19:
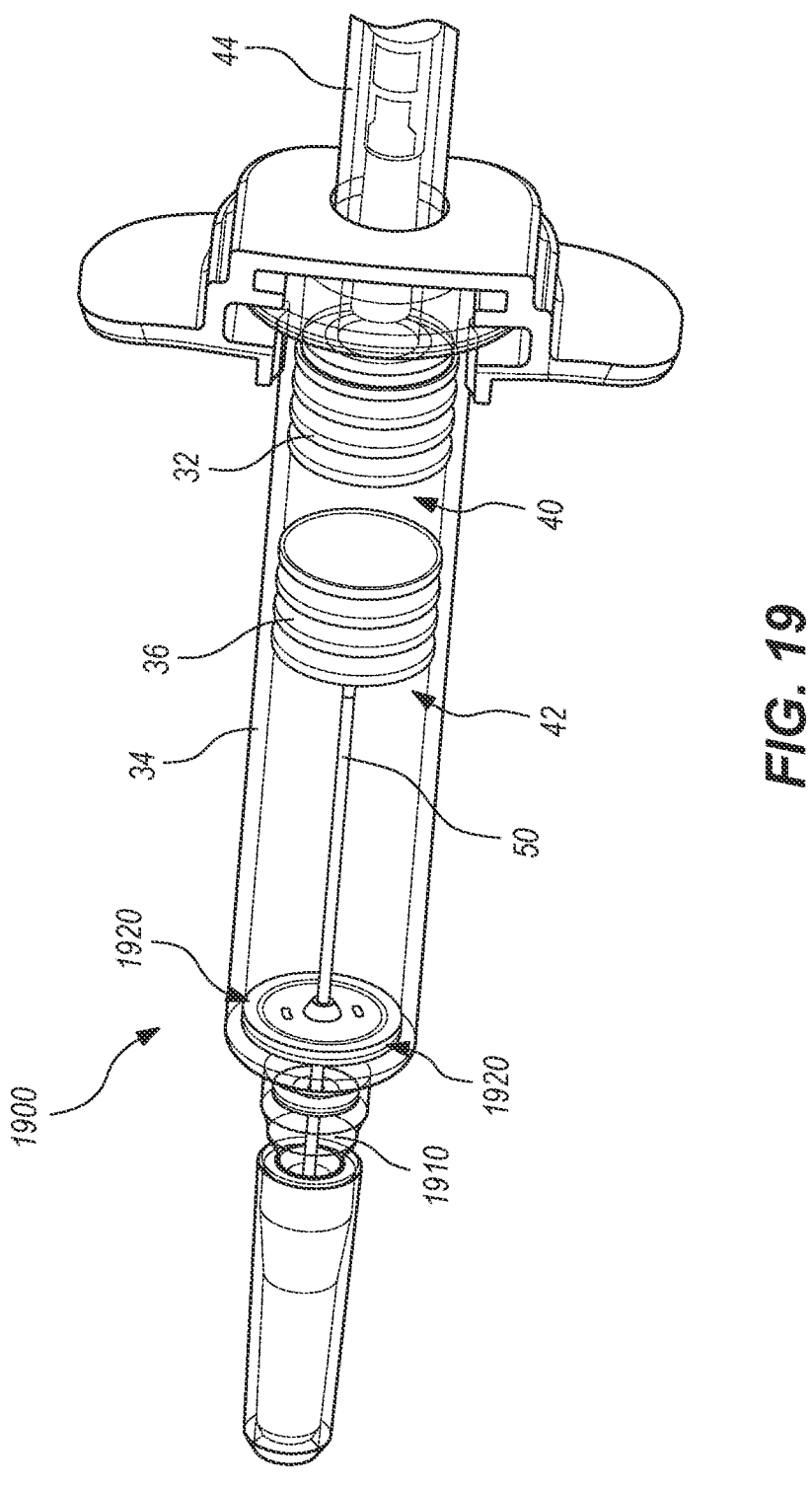
FIGS. 19 to 22 are detailed perspective views (FIGS. 19 to 21) and longitudinal cross-section views (FIG. 22) illustrating various aspects of syringe based dual chamber safe injection systems wherein a distal needle end/tip may be withdrawn into a protected configuration after use according to some embodiments.
Figure 20:
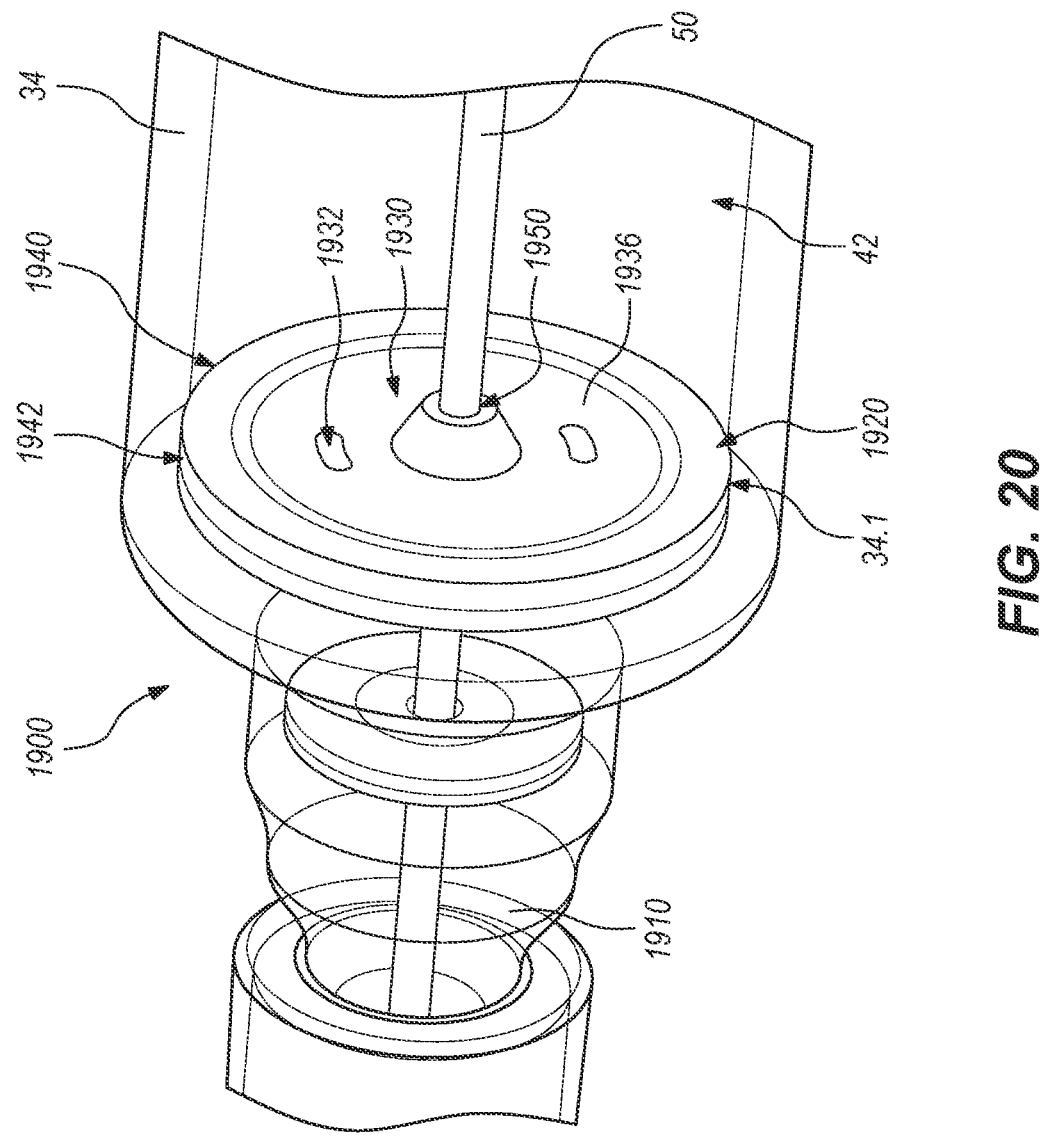
Figure 21:
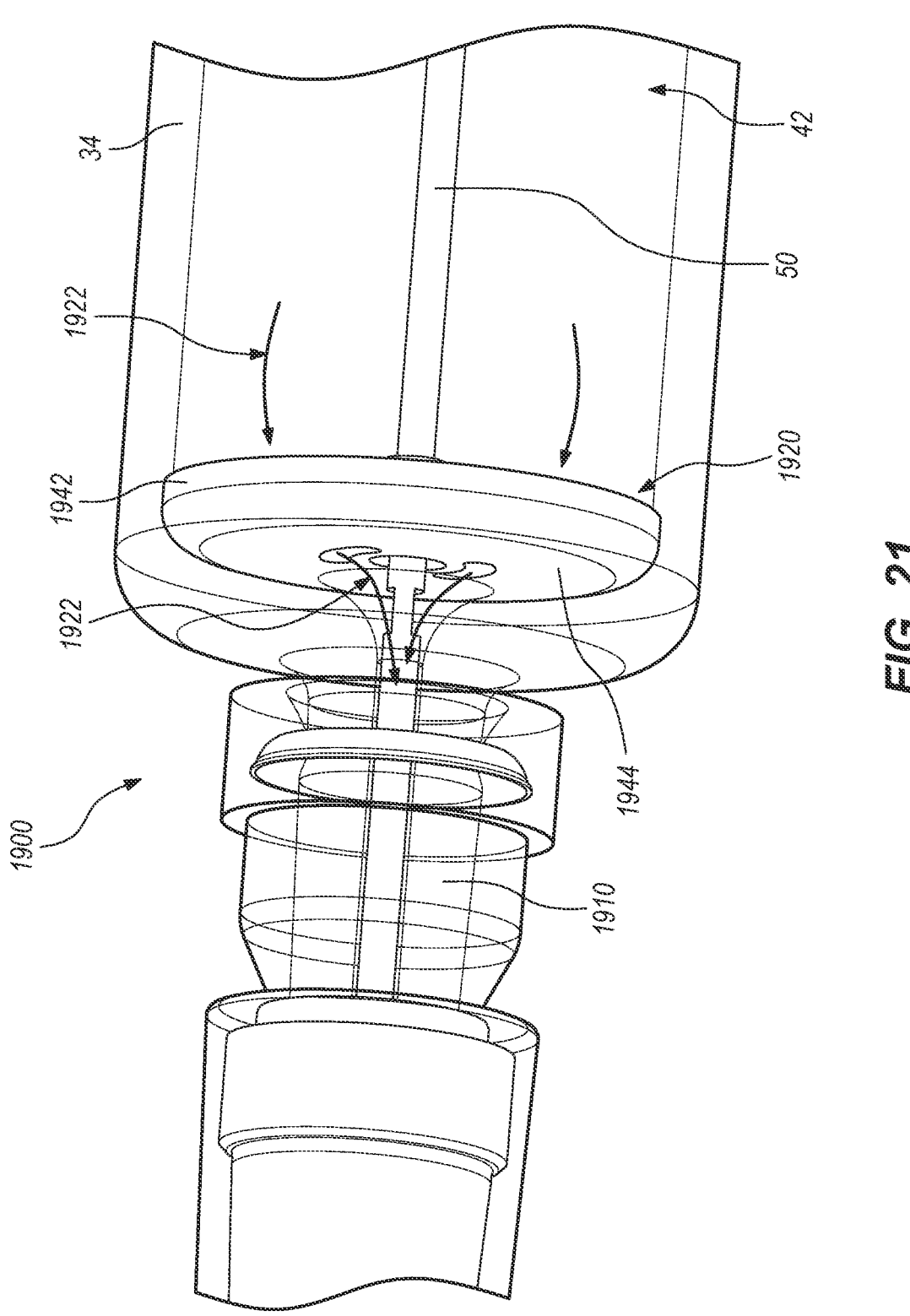
Figure 22:
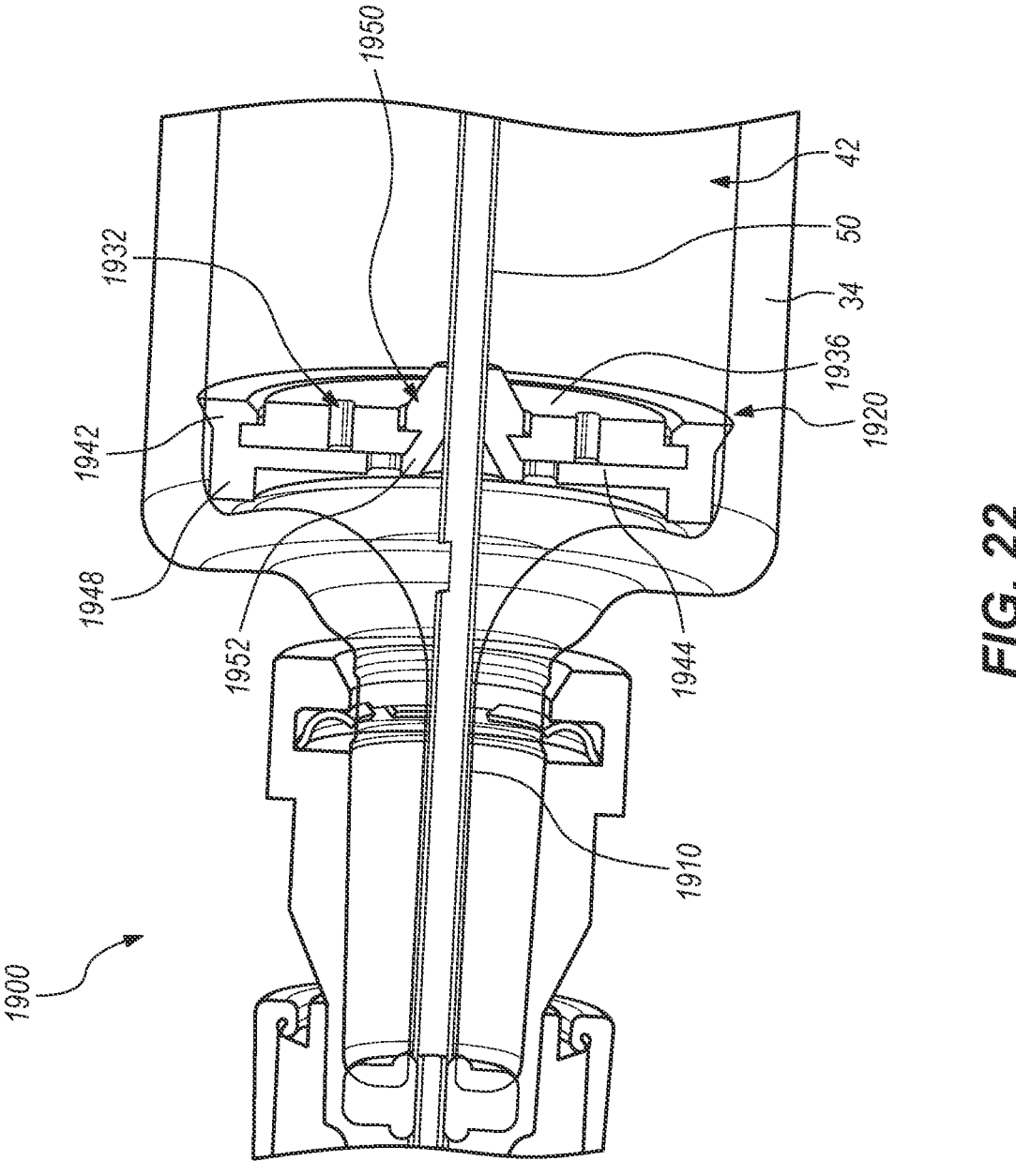

FIGS. 19 to 22 depict a dual chamber injection system (1900) having a valve (1920) disposed therein according to some embodiments. FIGS. 19, 20, and 22 depict the valve (1920) in a biased closed configuration. FIG. 21 depicts the valve (1920) in an open configuration. The valve (1920) includes a rigid member (1930) and an elastic member (1940). The rigid member (1930) defines a pair of ports (1932) and an annular portion (1936). The elastic member (1940) defines a circumferential gasket (1942) and an annular flap (1944). The circumferential gasket (1942) extends from the outer circumference of the annular flap (1944) such that the elastic member (1940) wraps around the annular portion (1936) of the rigid member (1930). The circumferential gasket (1942) is configured to form a fluid tight seal with a circumferential inner surface (34.1) of the injection system body (34).

The annular flap (1944) in the elastic member (1940) is biased to seal/close the pair of ports (1932) in the rigid member (1930). The ports (1932) are also configured to change into an open configuration with increased pressure (e.g., greater than atmospheric pressure) in the distal drug chamber (42) to open a flow path (1922; see FIG. 21) to allow a liquid (e.g., the mixed medicine) to pass through the valve (1920).

The circumferential gasket (1942) is also configured to exert a frictional force against the circumferential inner surface (34.1) of the injection system body (34) to couple the valve (1920) to the injection system body (34). The elastic member (1940) also defines a distally facing annular bump (1948; see FIG. 22) configured to provide sufficient space (1928) for the valve (1920) to open.

The valve (1920) depicted in FIGS. 19 to 22 is configured for use with a safe injection system, in which the fluid conveying member (50) is retractable into the injection system body (34) such that a sharp distal end (not shown) of a needle fluidly coupled to the fluid conveying member (50) is safely disposed inside of the injection system body (34) as shown in FIGS. 7O and 7P. As such, the valve (1920) includes a central seal (1950; see FIG. 22) configured to form a fluid tight seal against an outer longitudinal surface of the fluid conveying member (50). The fluid tight seal between the central seal (1950) and the fluid conveying member (50) is a light interference fit that minimizes or prevents substances from passing therethrough while allowing the fluid conveying member (50) to be withdrawn through the central seal (1950) during retraction. The central seal (1950) also includes a distally facing funnel (1952) configured to guide a proximal end of the fluid conveying member (50) into the central seal (1950) during assembly.

Exemplary Bushing with Insert in Dual Chamber Injection Systems

Figure 23:
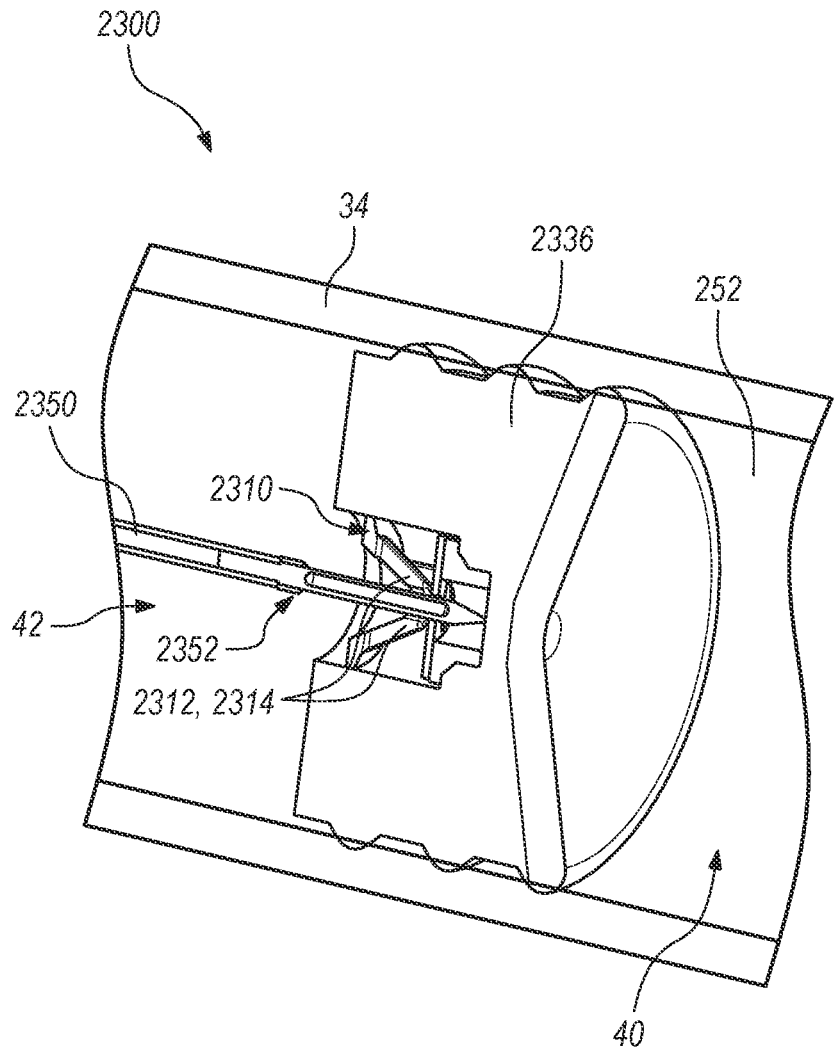
FIGS. 23 and 24 are detailed longitudinal cross-section views illustrating various aspects of syringe based dual chamber injection systems with a metal insert according to some embodiments.
Figure 24:
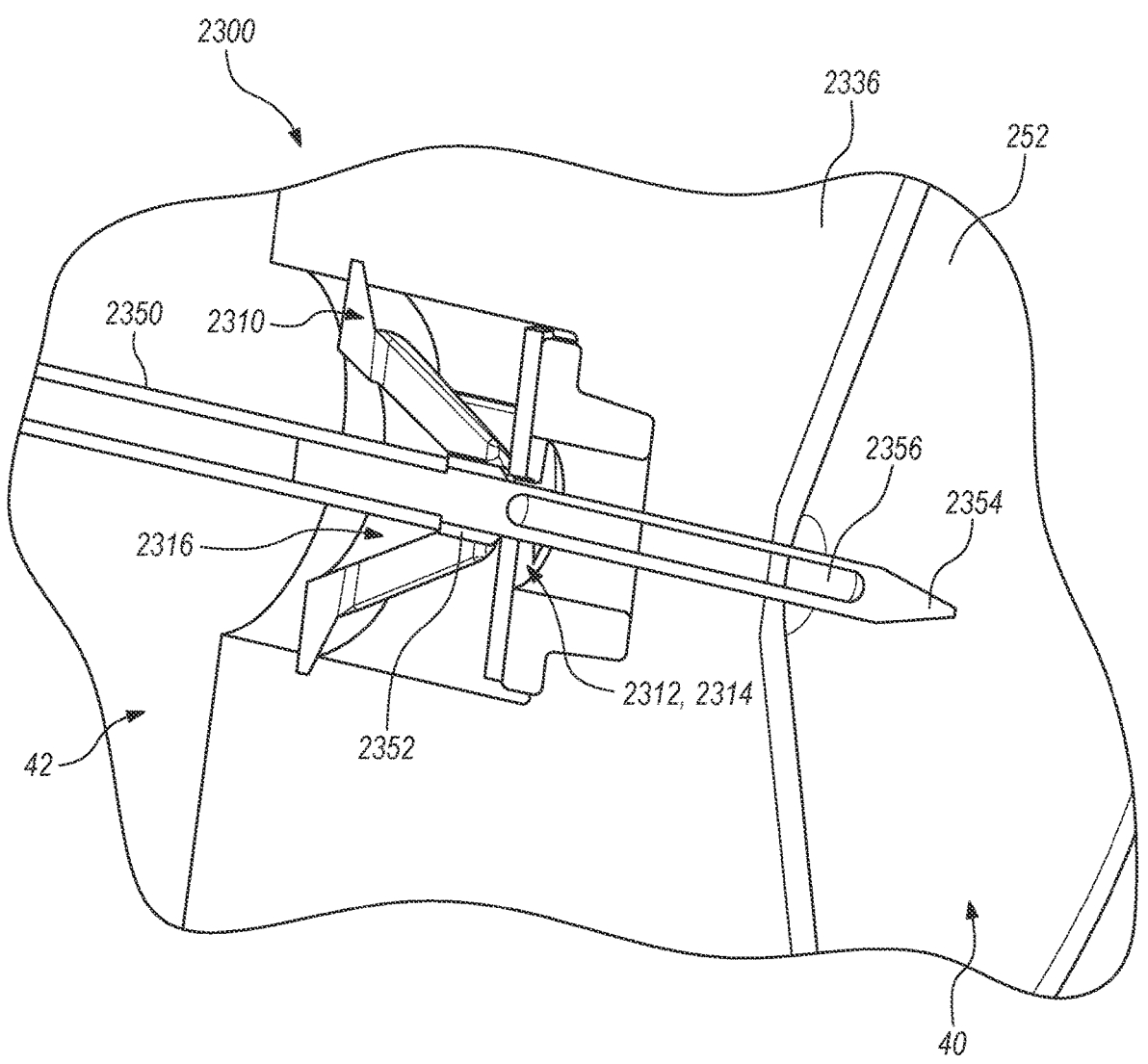
Figure 25:
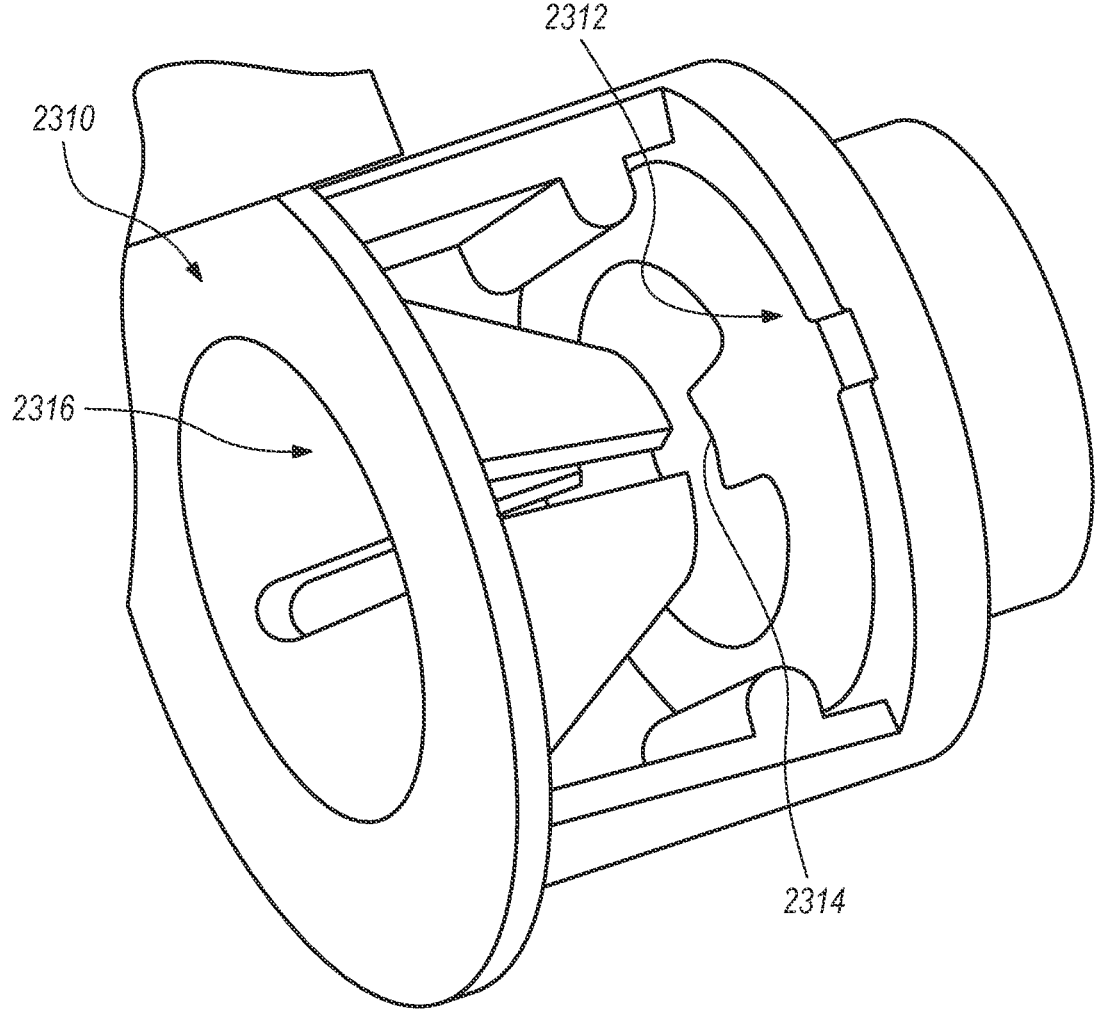
FIG. 25 is a photograph illustrating various aspects of syringe based dual chamber injection systems with a metal insert according to some embodiments.

FIGS. 23 to 25 depict a prefilled dual chamber safe injection system (2300) according to some embodiments. The system (2300) includes a stopper bushing (2310) having an insert (2312) disposed therein (see FIGS. 23 and 24). The insert (2312) a pair of fingers (2314) configured to interact with a shoulder (2352) formed on the fluid conveying member (2350) to provide resistance to distal movement of the distal stopper member (2336) relative to the fluid conveying member (2350) (see FIG. 24).

The interaction between the fingers (2314) of the insert (2312) and the shoulder (2352) maintains the distal stopper member (2336) in a transfer position during transfer of the liquid first medicine component from the proximal drug chamber (40) to the distal drug chamber (42). This interaction allows the user to apply a wider range of force to the plunger member to transfer the liquid while minimizing the risk of premature movement of the distal stopper member (36).

FIG. 23 shows a distal stopper member (36) having a stopper bushing (2310) with an insert (2312) and defining an alignment funnel (2316). In The alignment funnel (2316) is configured to guide a proximal end of the fluid conveying member (2350) into the insert (2312). FIG. 23 shows the storage/transport configuration of the system (2300). In this configuration, the sharpened proximal end (2354) of the fluid conveying member (2350) is disposed adjacent to and partially within the insert (2312). Various properties of the proximal end (2354) and the insert (2312) (e.g., geometric, material, etc.) can be modified to modulate the force required to push the proximal end (2354) to pierce the distal stopper member (2336). In some embodiments, the force required to push the proximal end (2354) to pierce the distal stopper member (2336) is from about 2 pounds to about 5 pounds. This allows the prefilled dual chamber system (2300) to be stored while minimizing the risk of premature movement of the distal stopper member (2336), which can render the system (2300) unusable.

FIG. 24 shows the transfer configuration of the system (2300). In this configuration, the distal stopper member (2336) has been pushed distally past the sharpened proximal end (2354) of the fluid conveying member (2350) by user provided force on the plunger member. A proximal end of a groove (2656) in the fluid conveying member (2350) is disposed in the proximal drug chamber (40) allowing liquid to transfer from the proximal drug chamber (40) to the distal drug chamber (42). In this configuration, a shoulder (2352) on the fluid conveying member (2350) is disposed adjacent to the fingers (2314) of the insert (2312). Various properties of the shoulder (2352) and the insert (2312) (e.g., geometric, material, etc.) can be modified to modulate the force required to push the shoulder (2352) past the fingers (2314) of the insert (2312). In some embodiments, the force required to push the shoulder (2352) past the insert (2312) is from about 2 pounds to about 5 pounds. While the interaction between the shoulder (2352) and the insert (2312) holds the system (2300) in the transfer configuration depicted in FIG. 24, pressure applied to the plunger member will aid liquid transfer from the proximal drug chamber (40) to the distal drug chamber (42). The force required to overcome the interference between the shoulder (2352) and the insert (2312) provides more latitude for a user to press the plunger member to aid in the liquid transfer. This increases the chances of complete liquid transfer.

The shoulder (2352) has a larger diameter than the portion of the fluid conveying member (2350) distal of the shoulder (2352). Accordingly, once the fingers (2314) of the insert (2312) moves distally past the shoulder (2352), the fingers (2314) do not generate significant friction against the fluid conveying member (2350). Further, the metal on metal interaction of the fingers (2314) against the fluid conveying member (2350) is more repeatable and generates fewer particles. In some embodiments, the insert (2312) is formed from a material with some degree of elasticity (e.g., annealed stainless steel) to further minimize the force on the fluid conveying member (2350) after clearing the shoulder (2352).

The predetermined amount of force can be modulated to accommodate a combination of the system function requirements and the aesthetic impression on the user. If the activation force is too low, it may work, but be too difficult for the user to apply the force lightly enough, and the user may overshoot. If the force is too high, the user may find that it is "too hard" to activate the system. Fortunately, the predetermined amount of force can be "tune" a range by modifying various component characteristics.

While the embodiments described above include dual chamber safety injection systems, the scope of the claims also include other multiple chamber safety injection systems. For multiple chamber safety injection systems with more than two chambers, more than two stopper members are inserted into an injection system body (e.g., syringe body, cartridge body, etc.) to define a corresponding number of chambers.

While the prefilled dual chamber safety injection systems depicted and described herein include syringes with staked needles, the various configurations/embodiments described herein (e.g., serial injection, detent dual chamber, threaded plunger member, and shielded and vented needle cover) can be used with cartridges an auto injector, and injection systems with Luer connectors, transfer pipes, and no needles such as those described in U.S. Utility patent application Ser. Nos. 15/801,281 and 15/801,259, which were previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, ETFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. An injection system, comprising:
a single piece injection system body defining only two openings, wherein the only two openings are a proximal opening at a proximal end thereof and a distal opening at a distal end thereof, and a distal needle interface at the distal end thereof;
a proximal stopper member and a distal stopper member disposed in the injection system body, forming a proximal drug chamber between the proximal stopper member and the distal stopper member and a distal drug chamber between the distal stopper member and the distal end of the injection system body;
a plunger member configured to be manipulated to insert the proximal stopper member relative to the injection system body; and a valve forming an openable barrier between the distal needle interface and at least a portion of the distal drug chamber,
wherein the valve is configured to allow flow from the portion of the distal drug chamber to the distal needle interface with increased pressure in the distal drug chamber, and
wherein the valve is disposed at the distal end of the single piece injection system body separate from the proximal stopper member and the distal stopper member.

2. The system of claim 1, further comprising an elongate fluid conveying member,
wherein the valve is configured to stabilize the elongate fluid conveying member in the distal drug chamber.

3. The system of claim 2, wherein the valve defines a central opening and includes a central seal,
wherein the fluid conveying member is configured to pass through the central opening, and
wherein the central seal is configured to form a fluid tight seal against an outer longitudinal surface of the fluid conveying member.

4. The system of claim 3, wherein the valve defines a distally facing circumferential wall configured to provide a space between the valve and the distal end of the injection system body.

5. The system of claim 1, wherein the valve comprises a circumferential gasket configured to form a fluid tight seal with an inner surface of the injection system body in the distal drug chamber.

6. The system of claim 5, wherein the circumferential gasket is made from an elastic material.

7. The system of claim 6, wherein the elastic material is rubber, thermoplastic elastomer, butyl rubber, or polyisoprene elastomer.

8. The system of claim 5, wherein the circumferential gasket is configured to couple the valve to the inner surface of the injection system body.

9. The system of claim 1, wherein the valve comprises a port configured to be opened by the increased pressure in the distal drug chamber.

10. The system of claim 1, wherein the valve comprises a rigid portion and an elastic portion.

11. The system of claim 10, wherein the rigid portion is made from cyclic olefin copolymer.

12. The system of claim 10, wherein the elastic portion is made from rubber, thermoplastic elastomer, butyl rubber, or polyisoprene elastomer.

13. The system of claim 10, wherein the elastic portion comprises:
an annular flap configured to be disposed adjacent a distal surface of the rigid portion; and
a circumferential gasket extending from an outer circumference of the annular flap,
wherein the circumferential gasket is configured to form a fluid tight seal with an inner surface of the injection system body in the distal drug chamber.

14. The system of claim 13, wherein the rigid portion comprises an annular portion,
wherein the annular portion defines a port extending therethrough, and
wherein the port is configured to be removably sealed by the annular flap of the elastic portion.

15. The system of claim 14, wherein the annular flap of the elastic portion is configured such that:
the annular flap is biased to removably seal the port; and the increased pressure in the distal drug chamber moves the annular flap away from the port defined by the annular portion of the rigid portion, thereby unsealing the port.

16. The system of claim 14, wherein the annular portion defines a raised annular wall surrounding the port and extending distally from a distal surface of the annular portion.

17. The system of claim 14, wherein the annular portion defines a distally extending dome.

18. The system of claim 10, wherein the rigid portion comprises a distally extending portion coupled to an annular portion.

19. The system of claim 18, wherein the distally extending portion is configured to interfere with the distal needle interface to provide a space between the valve and the distal end of the injection system body.

20. The system of claim 18, wherein the distally extending portion is configured to interfere with the distal needle interface to couple the valve to the injection system body such that a distal surface of a circumferential gasket of the valve is in contact with the distal end of the injection system body.

21. The system of claim 20, wherein the circumferential gasket is configured to form a fluid tight seal with an inner surface of the distal end of the injection system body.

22. The system of claim 20, wherein the circumferential gasket has an outer circumference smaller than an inner circumference of the injection system body.

23. The system of claim 20, wherein the distally extending portion is configured to interfere with the distal needle interface to provide a space between the valve and the distal end of the injection system body.

24. An injection system, comprising:

an injection system body defining a proximal opening at a proximal end thereof and a distal needle interface at a distal end thereof;

a proximal stopper member and a distal stopper member disposed in the injection system body, forming a proximal drug chamber between the proximal stopper member and the distal stopper member and a distal drug chamber between the distal stopper member and the distal end of the injection system body;

a plunger member configured to be manipulated to insert the proximal stopper member relative to the injection system body; and a valve forming an openable barrier between the distal needle interface and at least a portion of the distal drug chamber, wherein the valve defines a distally facing funnel configured to guide a proximal end of the fluid conveying member through the central seal during assembly of the injection system.

25. An injection system, comprising:

an injection system body defining a proximal opening at a proximal end thereof and a distal needle interface at a distal end thereof, a proximal stopper member and a distal stopper member disposed in the injection system body, forming a proximal drug chamber between the proximal stopper member and a distal stopper member and a distal drug chamber between the distal stopper member and the distal end of the injection system body;

a plunger member configured to be manipulated to insert the proximal stopper member relative to the injection system body;

an elongate fluid conveying member configured to at least partially pierce the distal stopper member to form a flow path from the distal drug chamber to the proximal drug chamber, the elongate fluid conveying member defining a circumferential shoulder; and an insert configured to be disposed in the distal stopper member, wherein the insert comprises a distally facing funnel and a pair of fingers configured to interfere with the circumferential shoulder on the elongate fluid conveying member to temporarily prevent distally directed motion of the distal stopper member relative to the elongate fluid conveying member while the flow path from the distal drug chamber to the proximal drug chamber is open wherein the pair of fingers are disposed proximally of the distally facing funnel.

* * * * *